US007642087B2

(12) United States Patent
Imoarai et al.

(10) Patent No.: US 7,642,087 B2
(45) Date of Patent: Jan. 5, 2010

(54) CHROMATOGRAPHY KIT, EXAMINATION CONTAINER, AND METHOD FOR MANUFACTURING THE SAME

(75) Inventors: Takeshi Imoarai, Kobe (JP); Shinya Nagai, Akashi (JP); Motoi Furutani, Akashi (JP); Kanako Horisaka, Akashi (JP)

(73) Assignee: Sysmex Corporation, Hyogo (JP)

( * ) Notice: Subject to any disclaimer, the term of this patent is extended or adjusted under 35 U.S.C. 154(b) by 228 days.

(21) Appl. No.: 11/527,562

(22) Filed: Sep. 27, 2006

(65) Prior Publication Data

US 2007/0178606 A1 Aug. 2, 2007

(30) Foreign Application Priority Data

Sep. 27, 2005 (JP) ............................ 2005-280587
Sep. 28, 2005 (JP) ............................ 2005-282399
Jul. 28, 2006 (JP) ............................ 2006-206619

(51) Int. Cl.
*C12M 1/34* (2006.01)
*C12M 3/00* (2006.01)

(52) U.S. Cl. ................. 435/287.2; 435/287.1; 435/970; 435/973; 435/875; 436/518; 436/514; 422/56; 422/57; 422/58; 422/59; 422/60; 422/61; 422/68.1; 422/102

(58) Field of Classification Search ............. 422/56–61, 422/68.1, 102; 435/287.1, 970, 287.2, 973, 435/875

See application file for complete search history.

(56) References Cited

U.S. PATENT DOCUMENTS

| | | | | |
|---|---|---|---|---|
| 3,776,220 | A * | 12/1973 | Monaghan | 600/572 |
| 4,387,725 | A * | 6/1983 | Mull | 600/572 |
| 5,712,172 | A | 1/1998 | Huang et al. | |
| 6,403,383 | B1 * | 6/2002 | Casterlin et al. | 436/518 |
| 6,461,873 | B1 * | 10/2002 | Catania et al. | 436/518 |
| 6,537,828 | B1 | 3/2003 | Nakaya et al. | |
| 2003/0190745 | A1 * | 10/2003 | Galloway et al. | 435/287.2 |

* cited by examiner

*Primary Examiner*—Bao-Thuy L Nguyen
(74) *Attorney, Agent, or Firm*—Sughrue Mion, PLLC

(57) ABSTRACT

An chromatography kit is described, a representative one of which includes: an examination container one end of which has an inlet for receiving a sample, and an chromatography examination strip used by inserting from the inlet into the examination container wherein the examination container comprises a prevention part for preventing from the adherence of the examination strip on the inner wall of the examination container.

7 Claims, 21 Drawing Sheets

[Fig. 1]
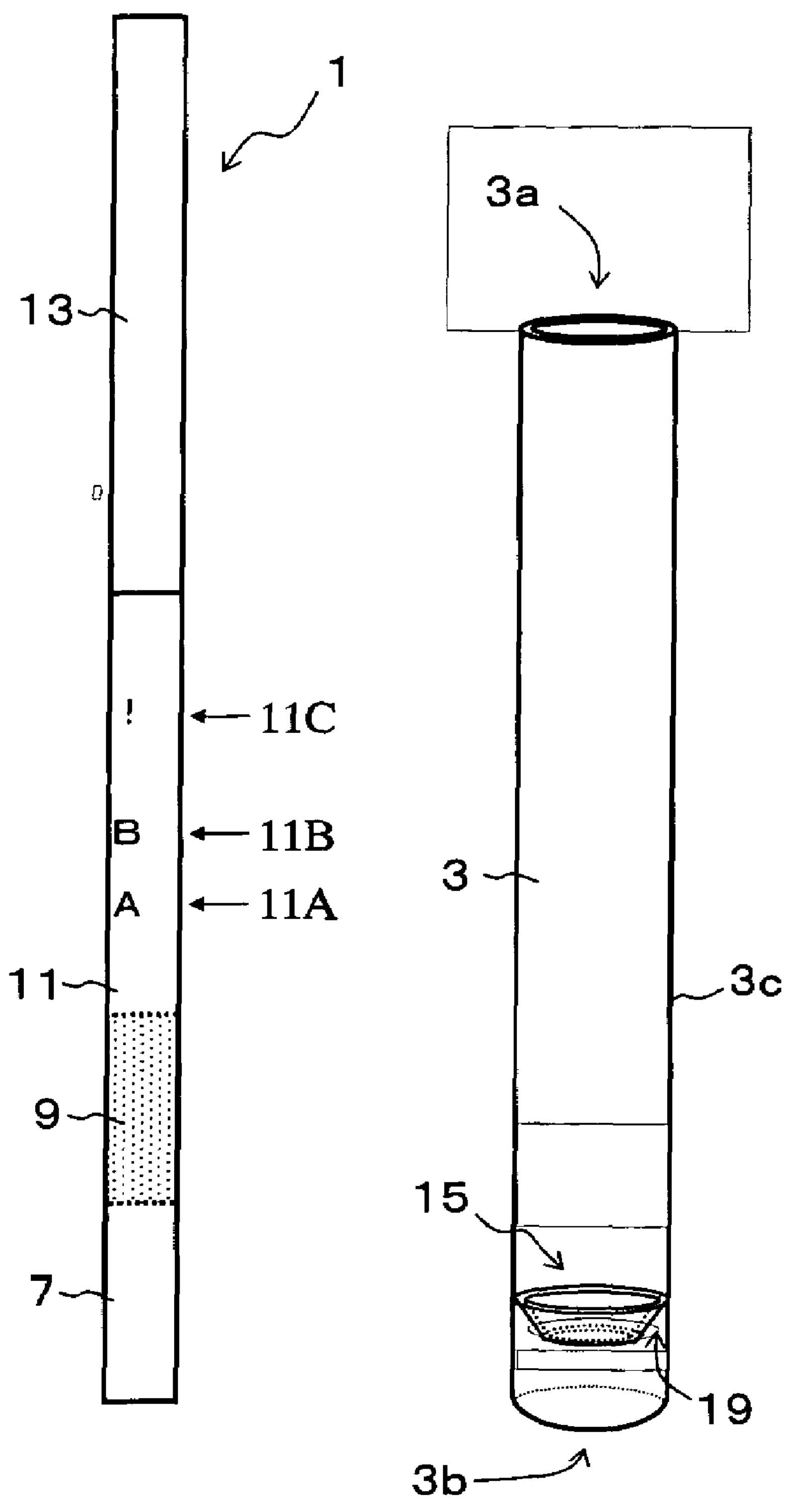

[Fig. 2]
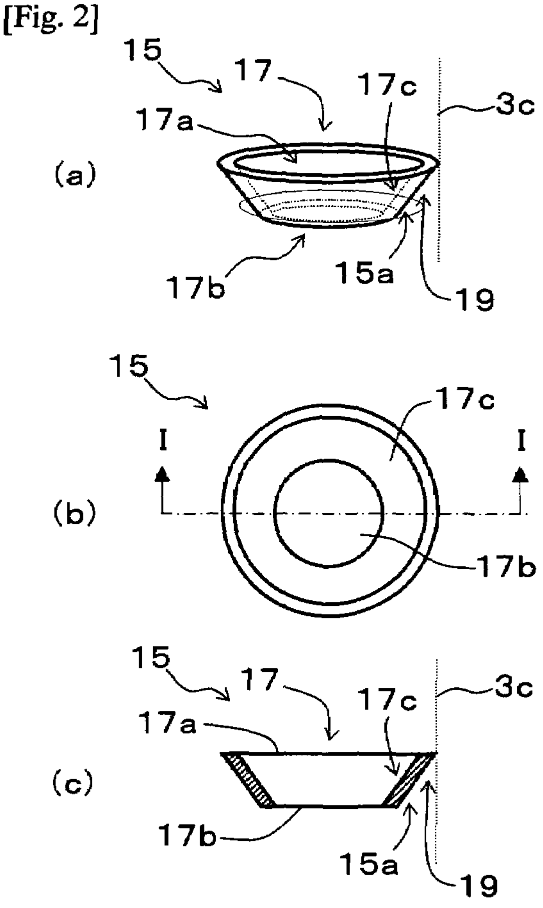
[Fig. 3]
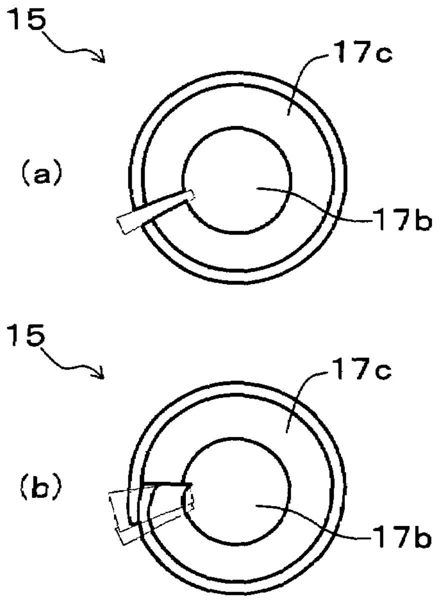

[Fig. 4]
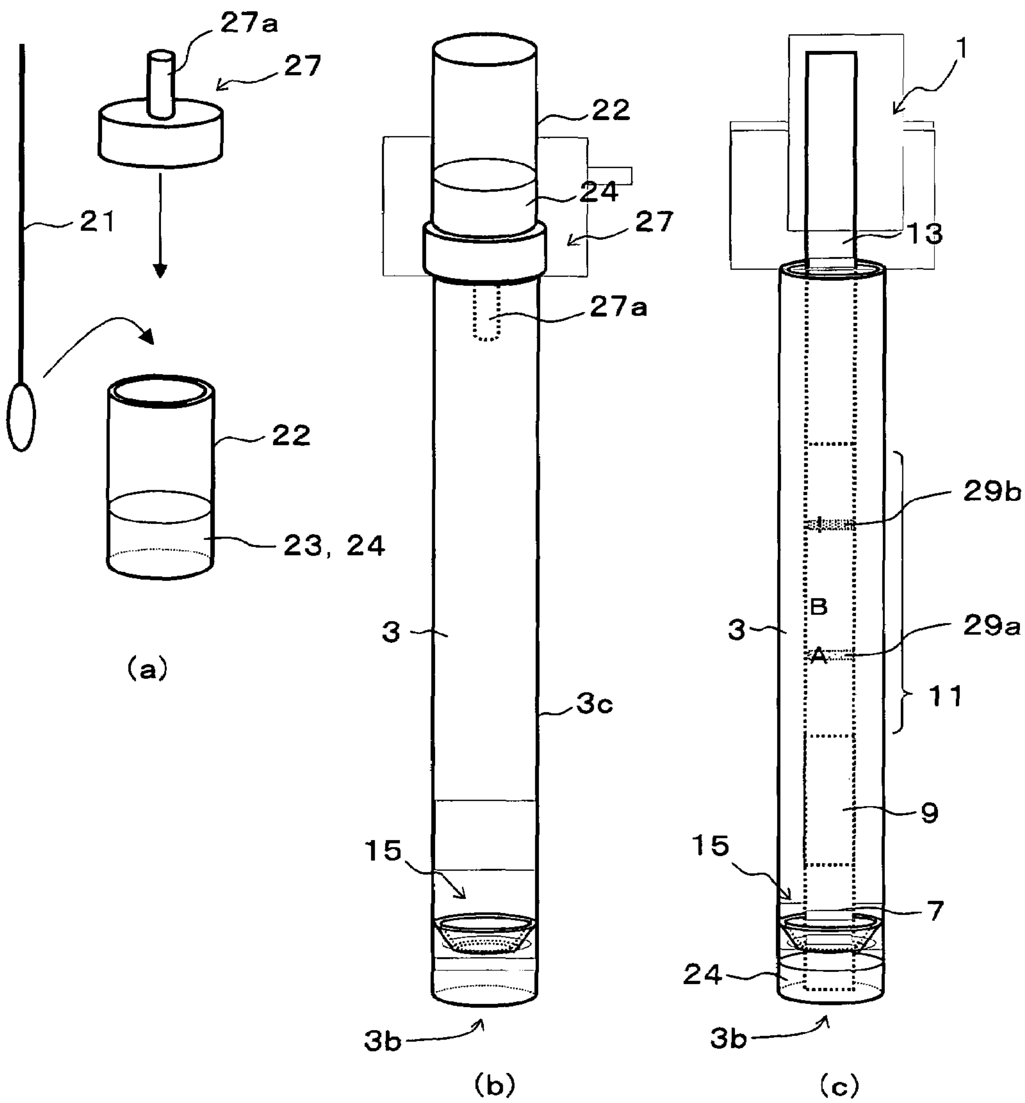

[Fig. 5]
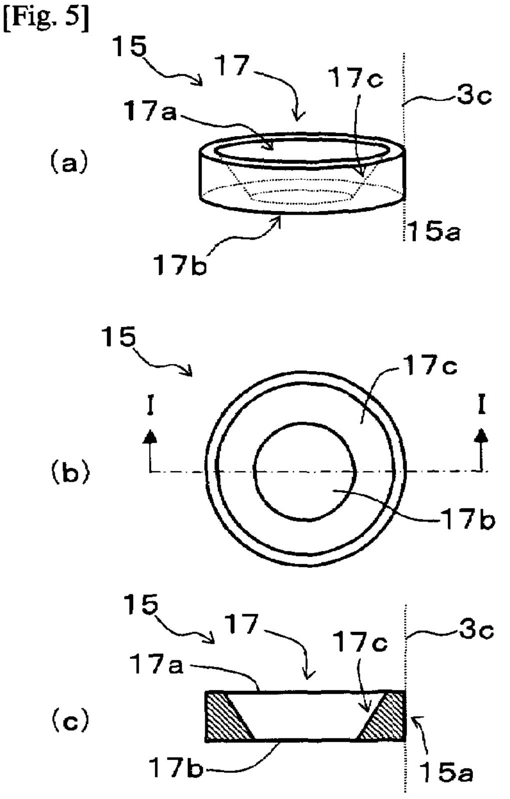
[Fig. 6]
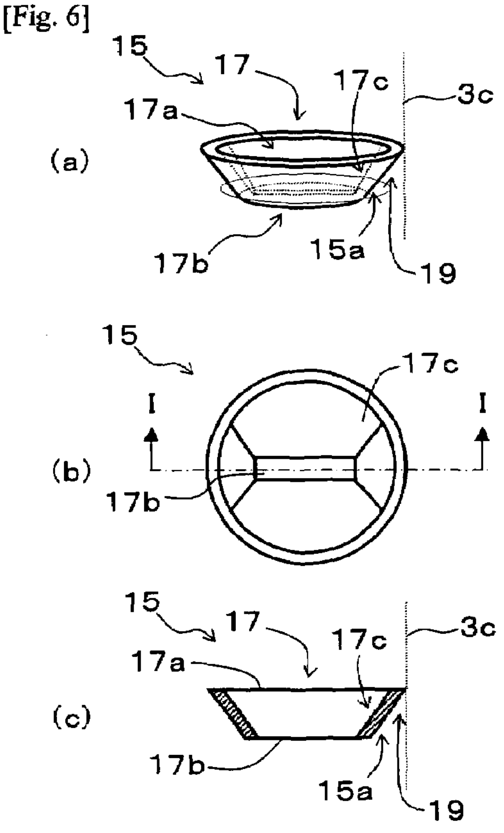

[Fig.7]
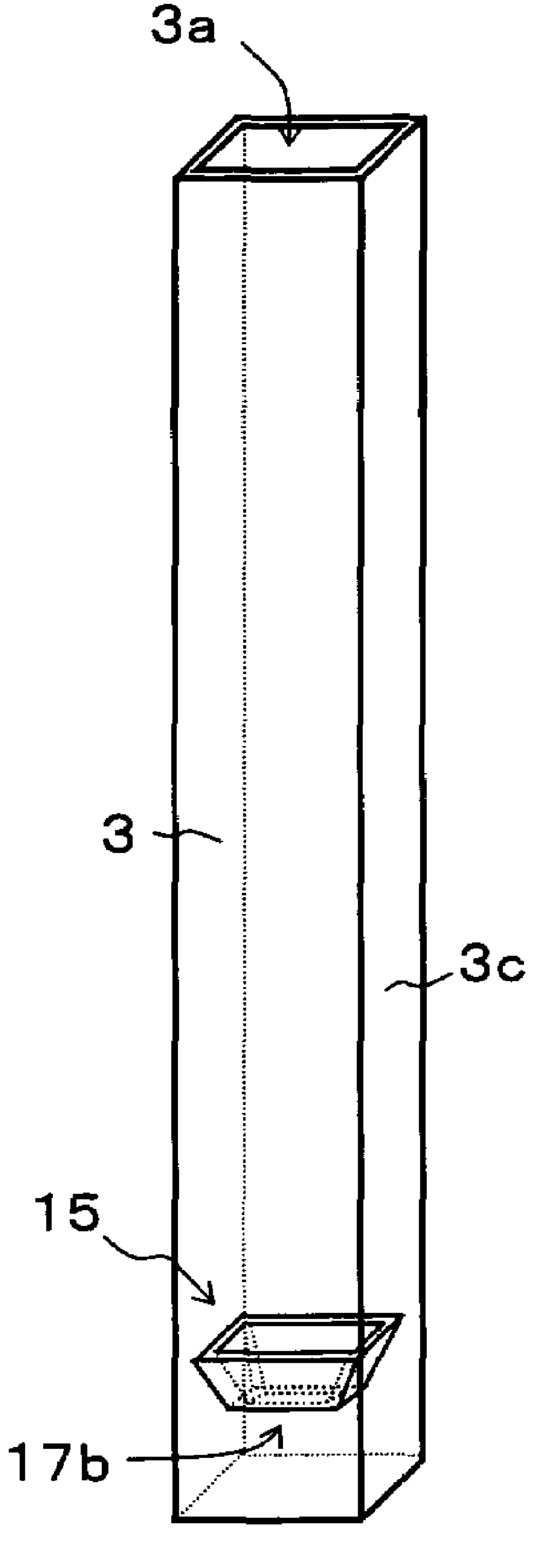

[Fig. 8]
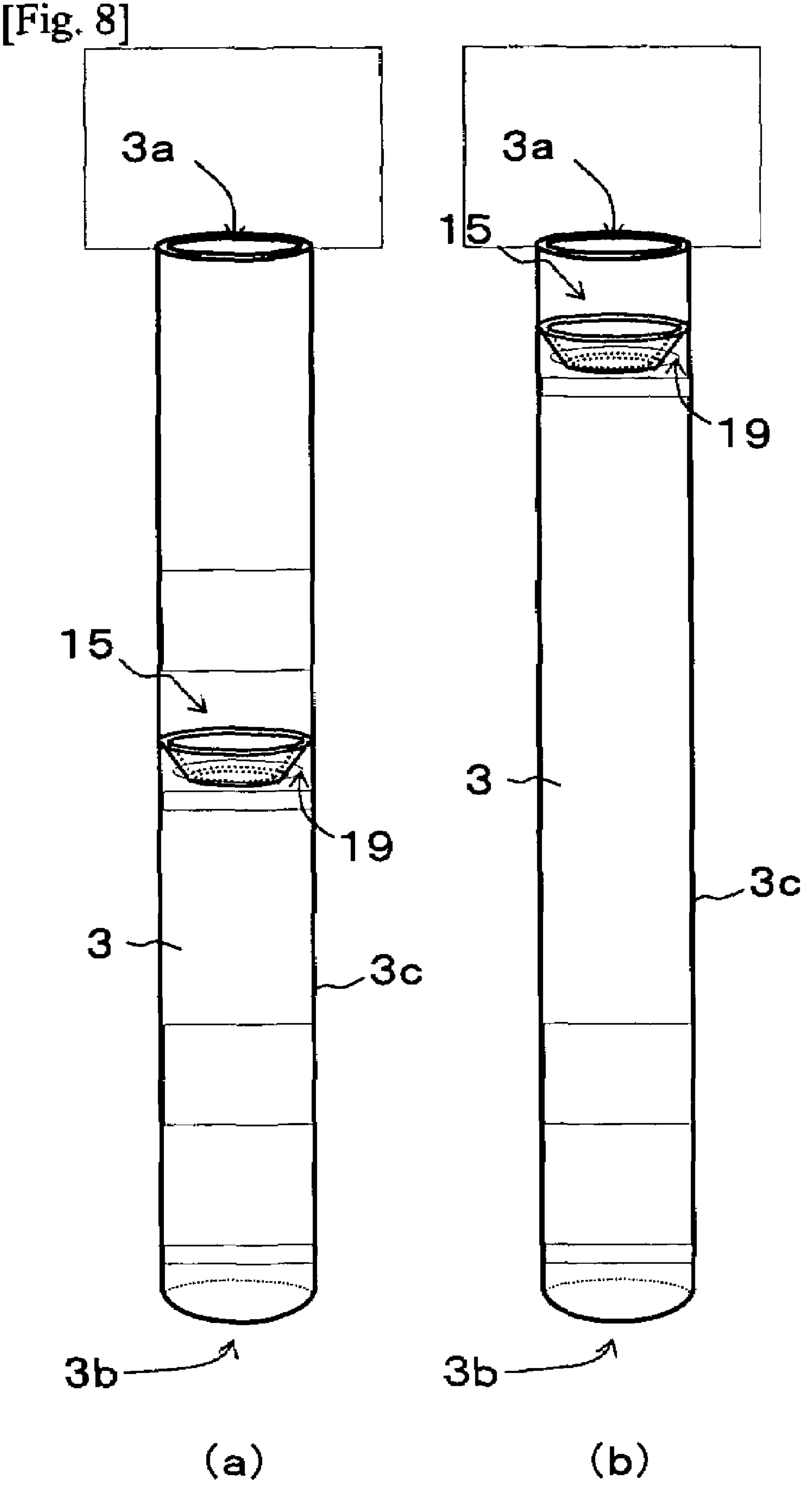

[Fig. 9]
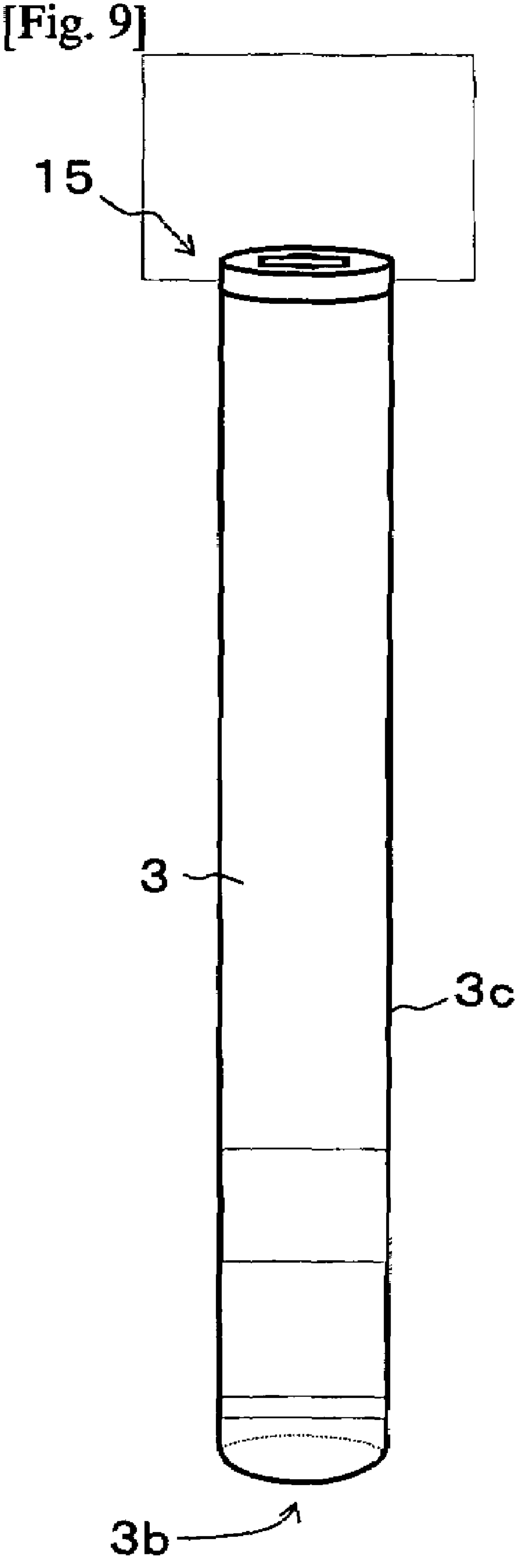

[Fig. 10]
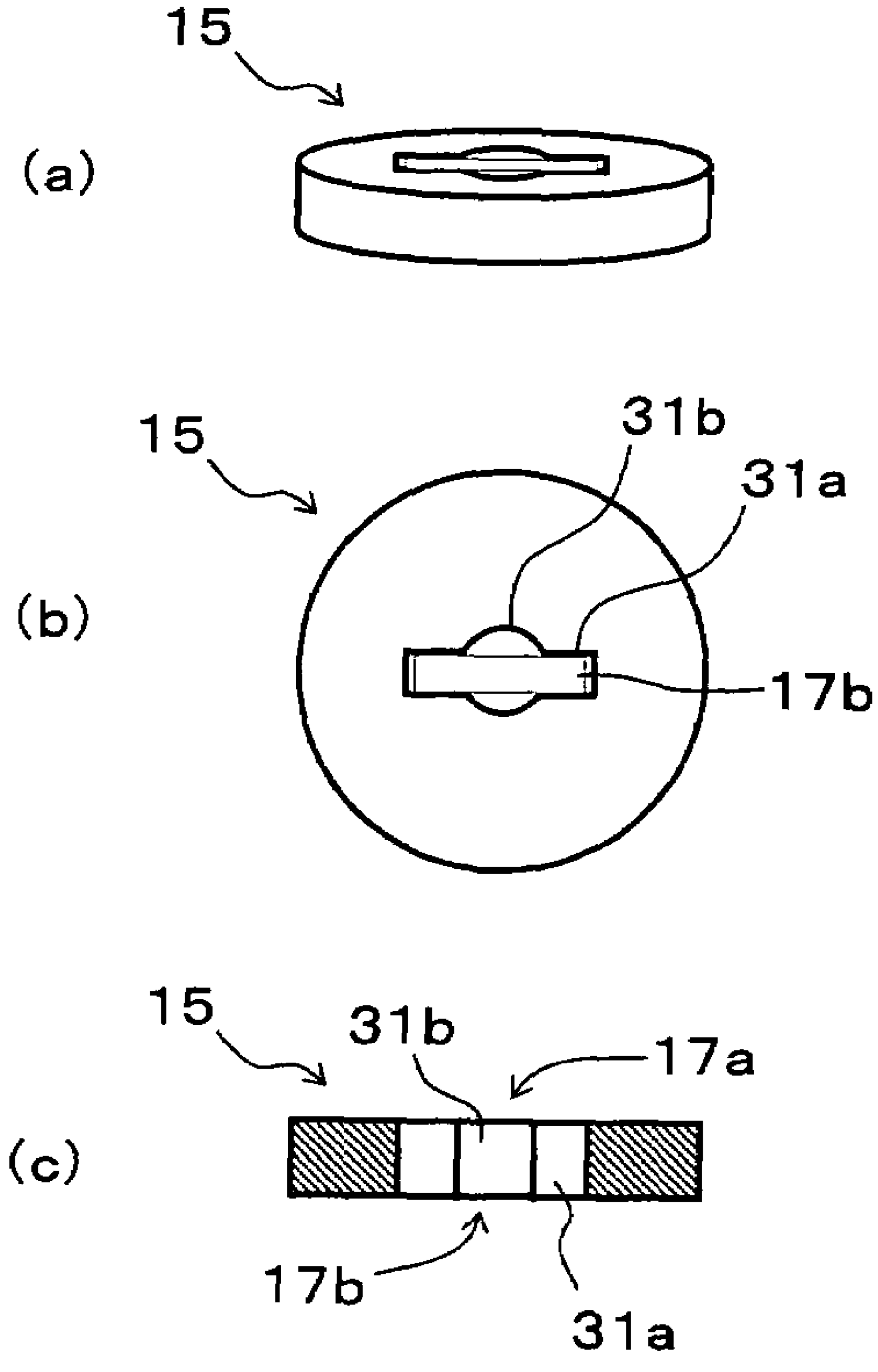

[Fig. 11]
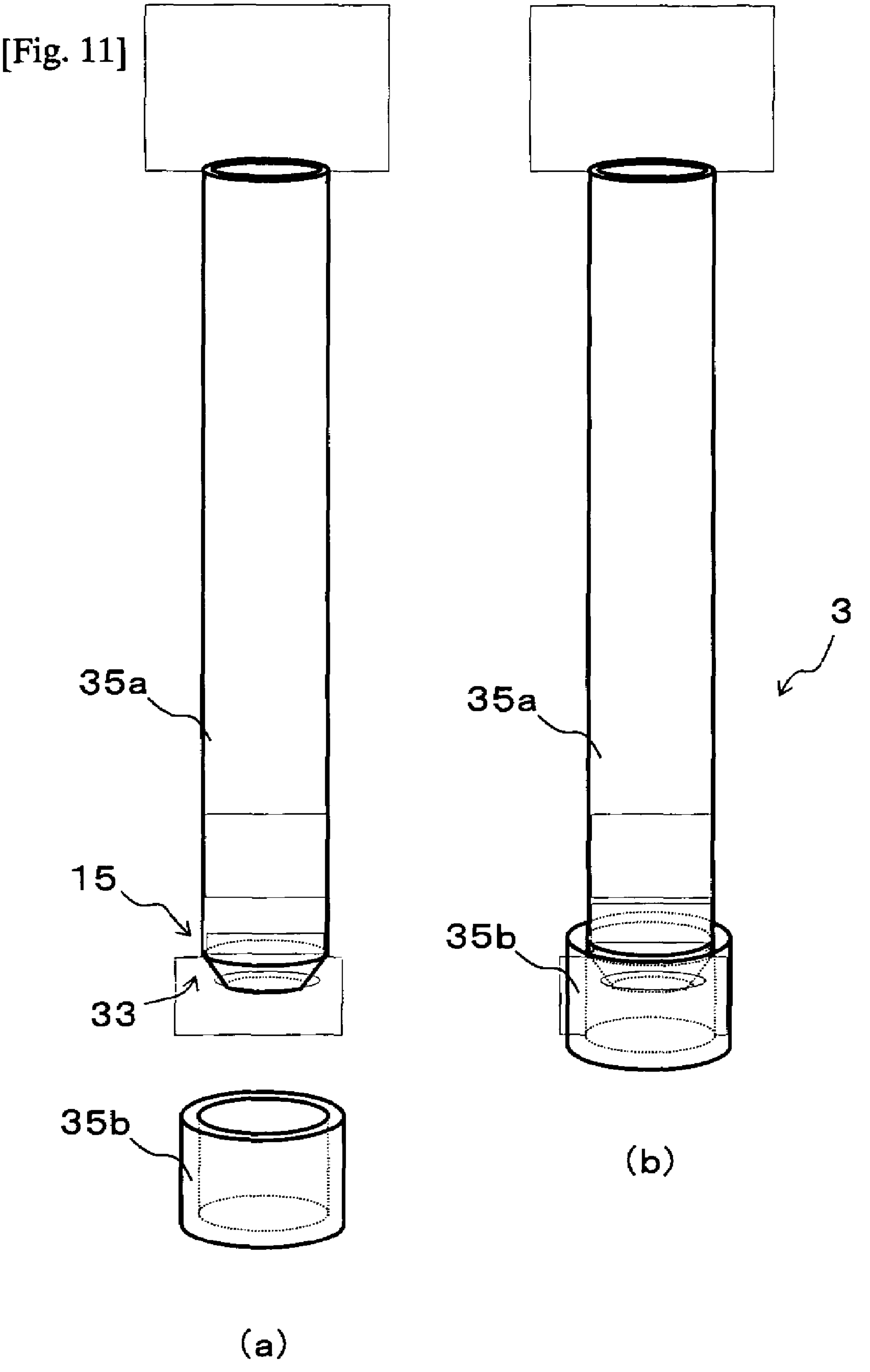

[Fig. 12]
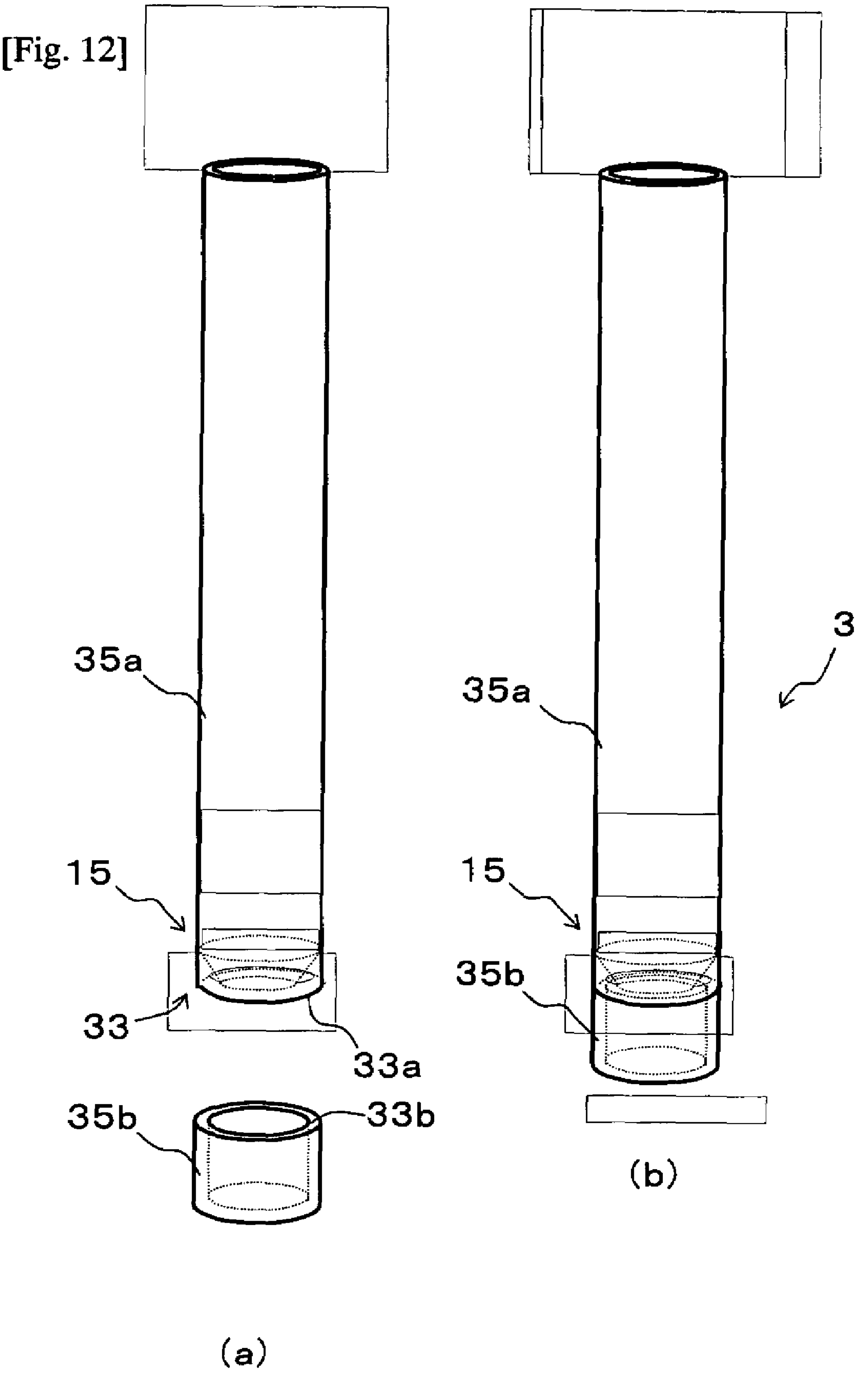

[Fig. 13]
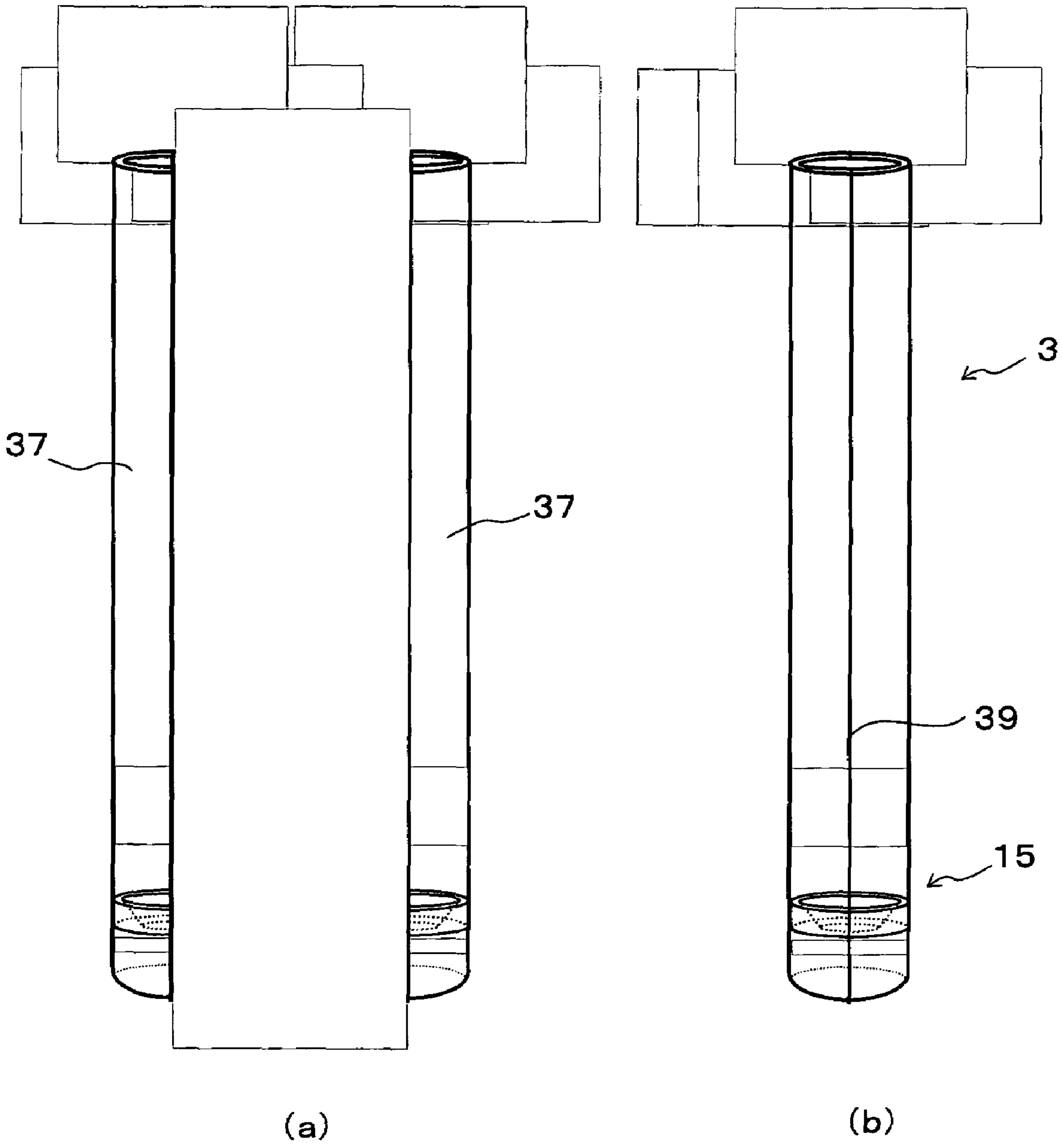

[Fig. 14]
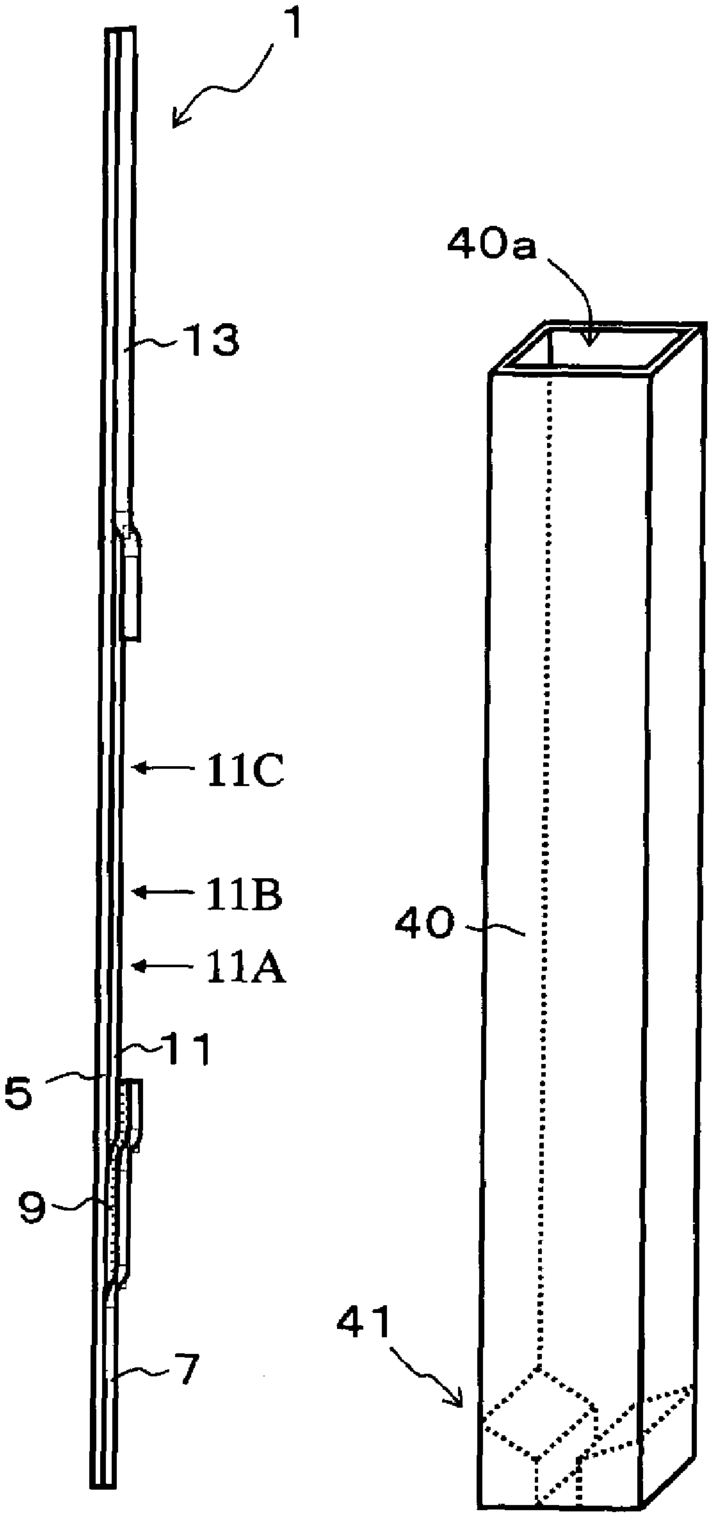

[Fig. 15]
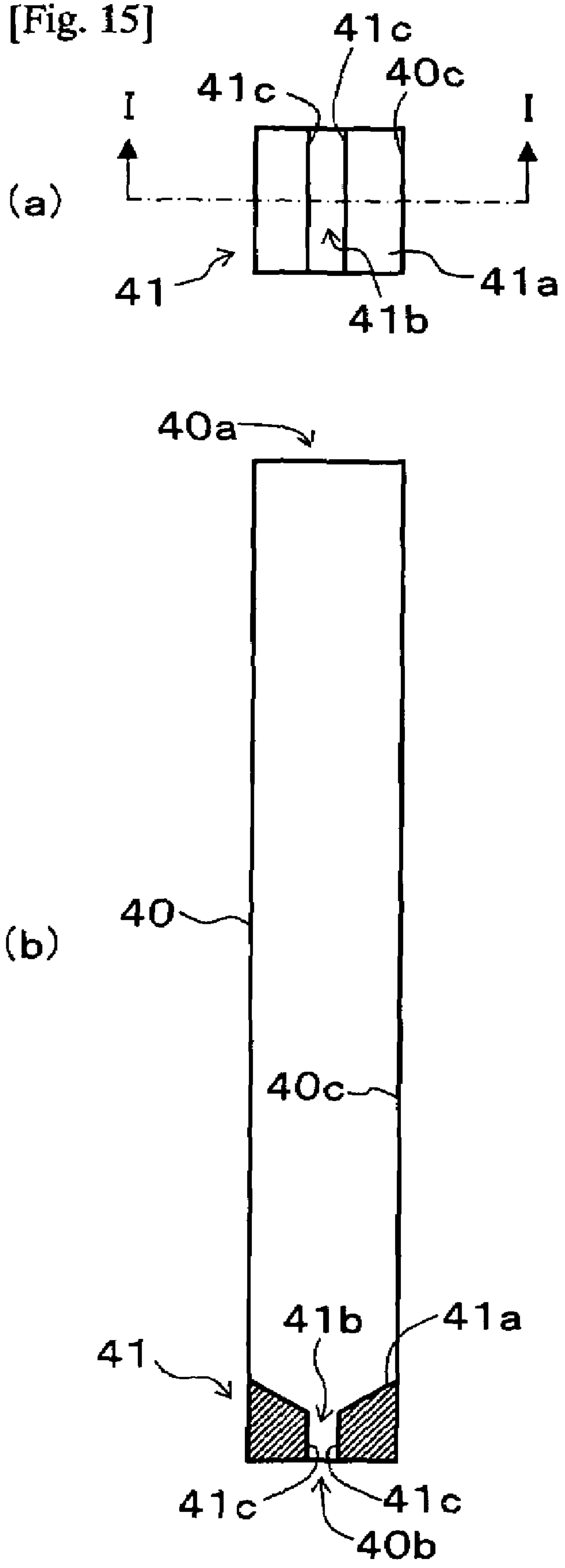

[Fig. 16]
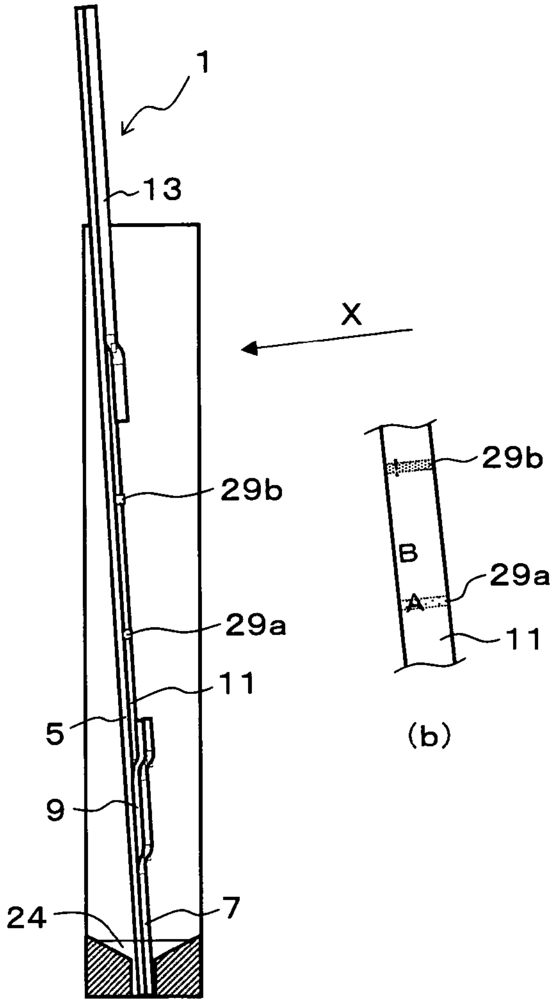
(a)
(b)
[Fig. 17]
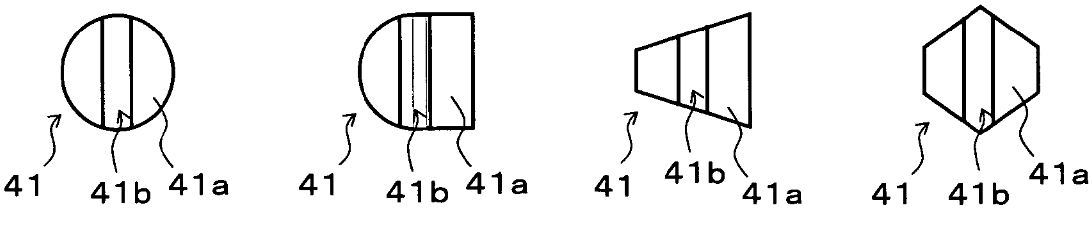
(a) (b) (c) (d)

[Fig. 18]
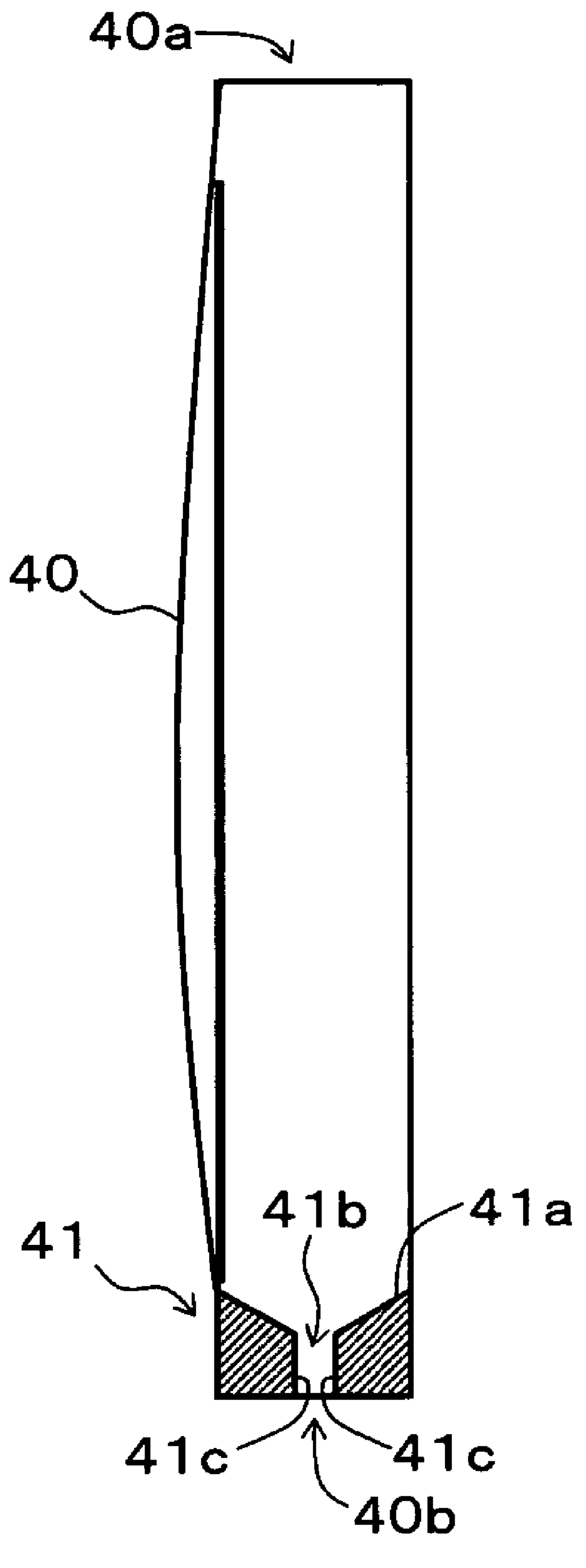

[Fig. 19]
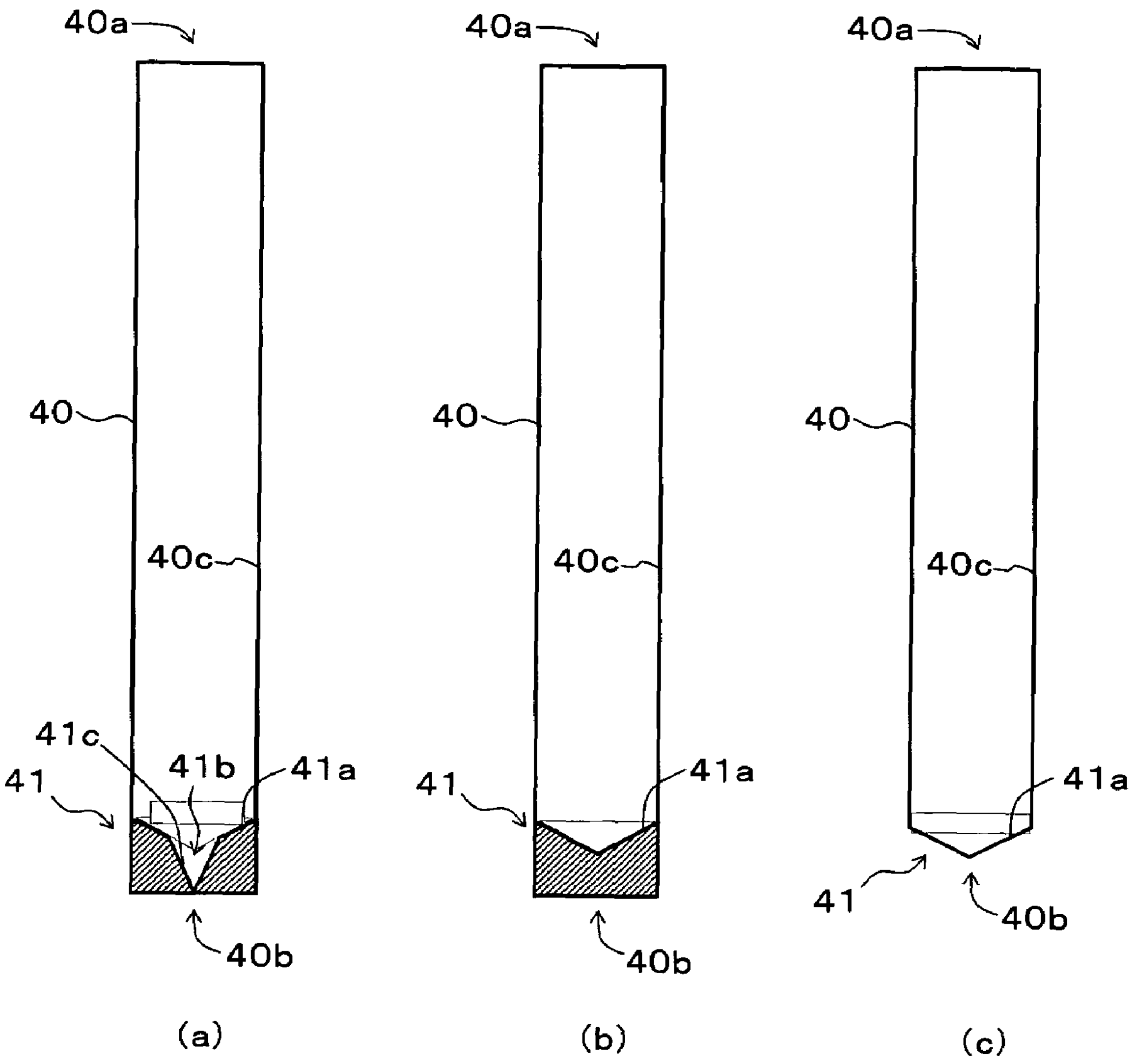

[Fig. 20]
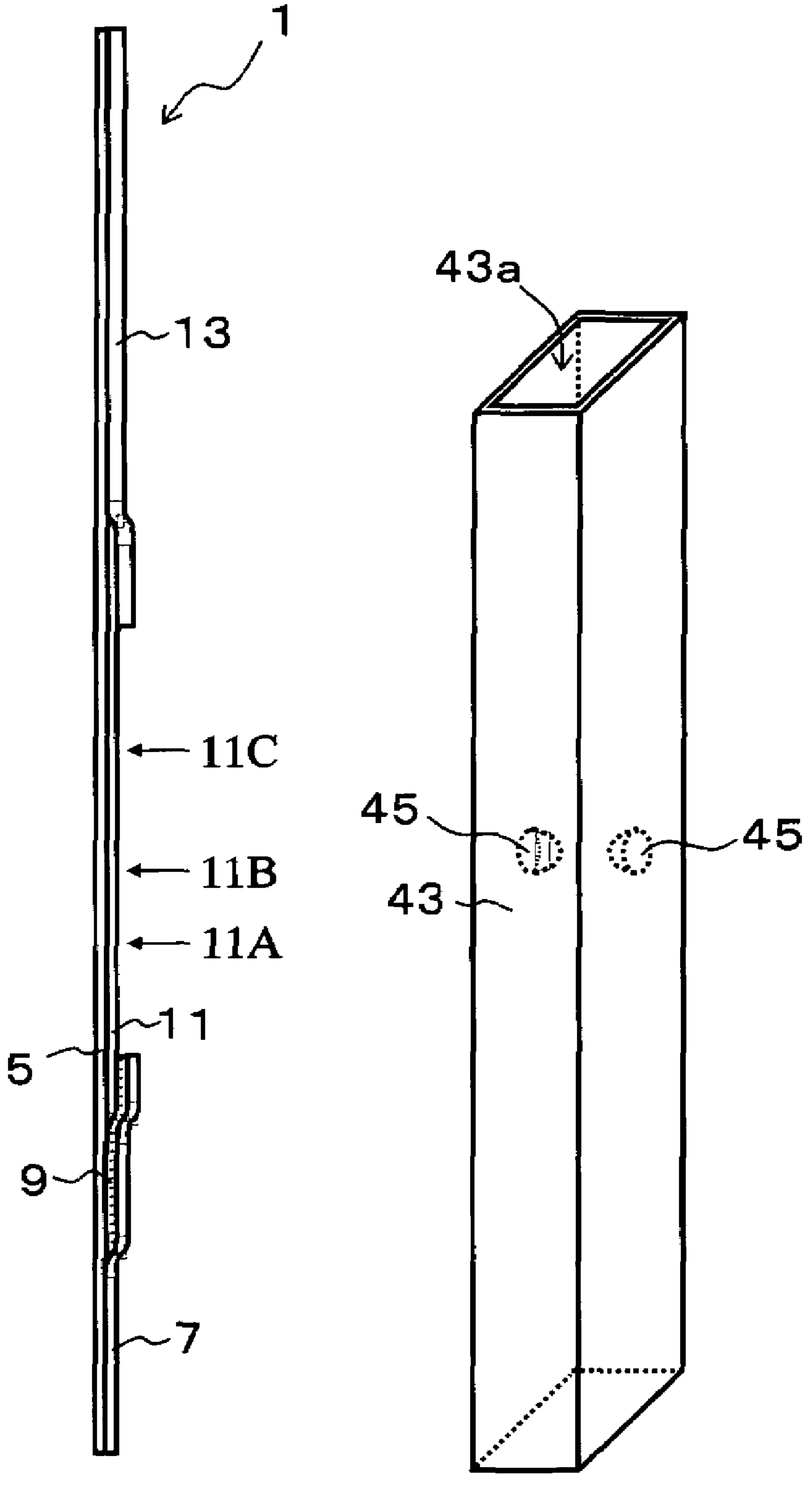

[Fig. 21]
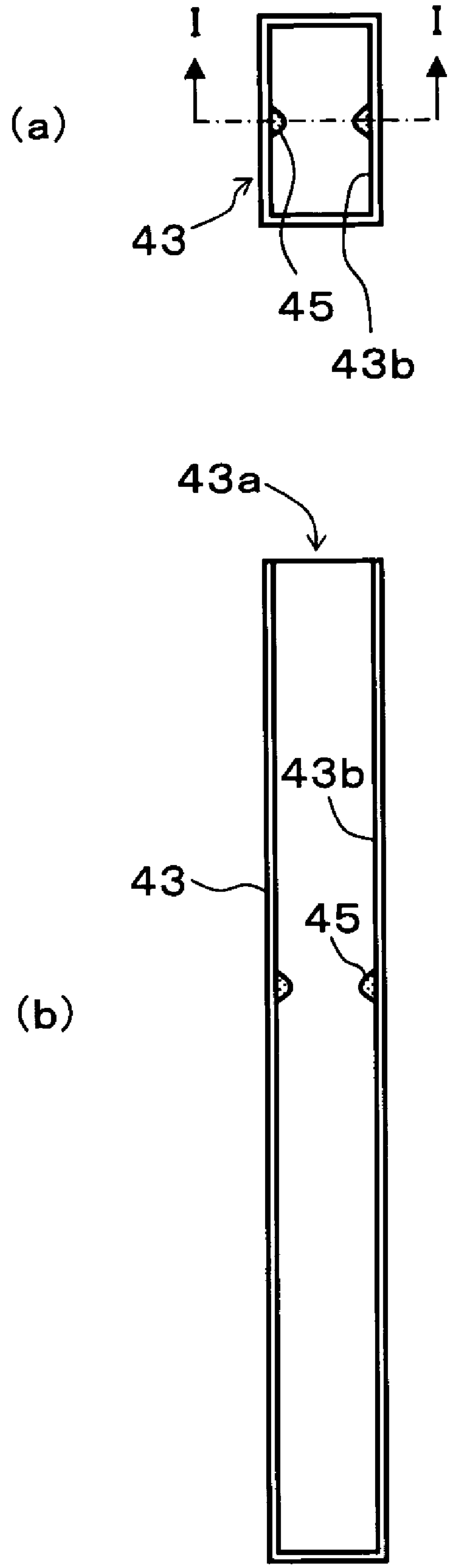

[Fig. 22]
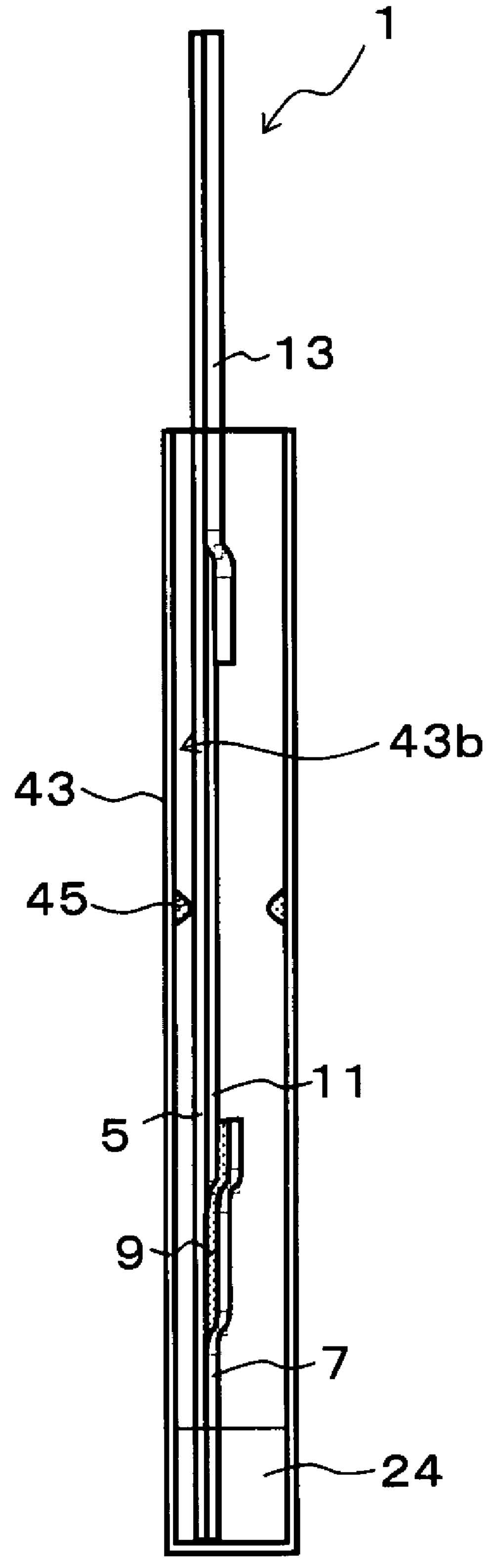

[Fig. 23]
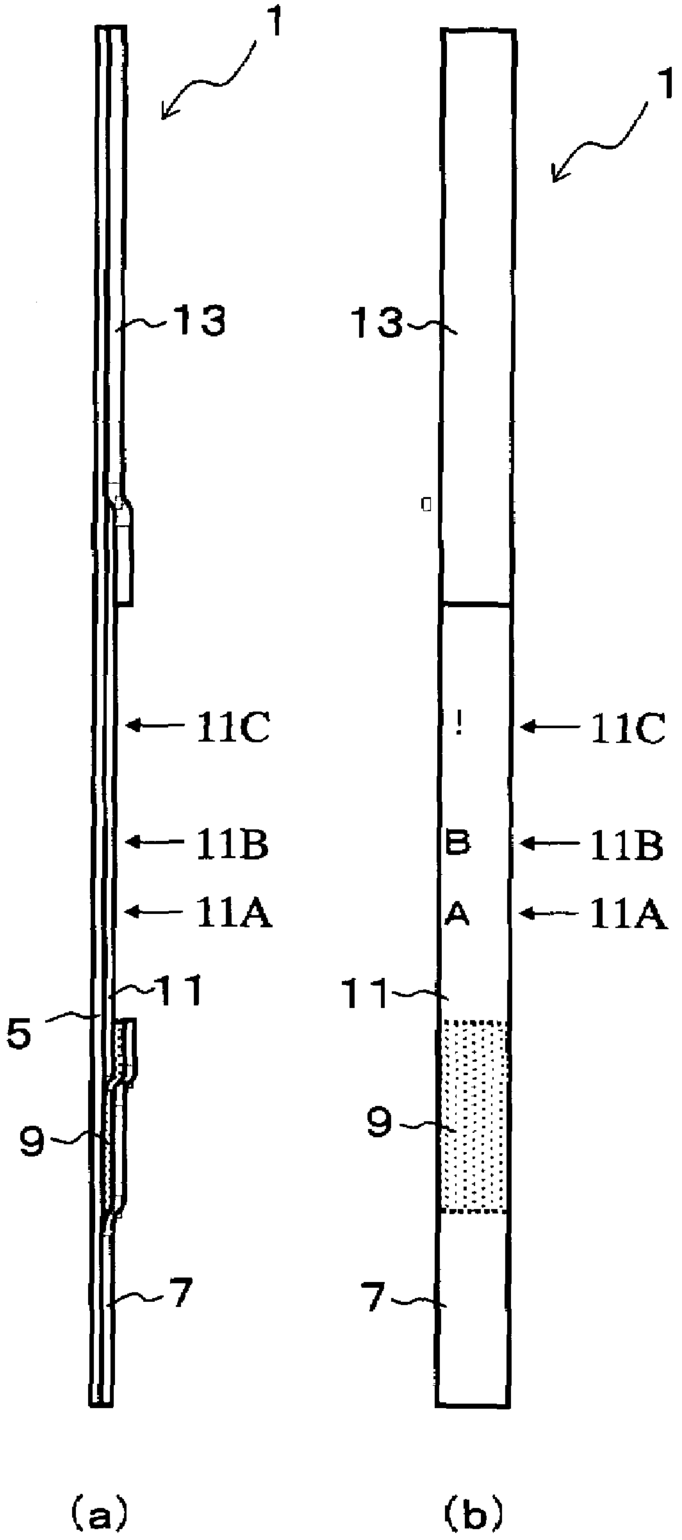

[Fig. 24]
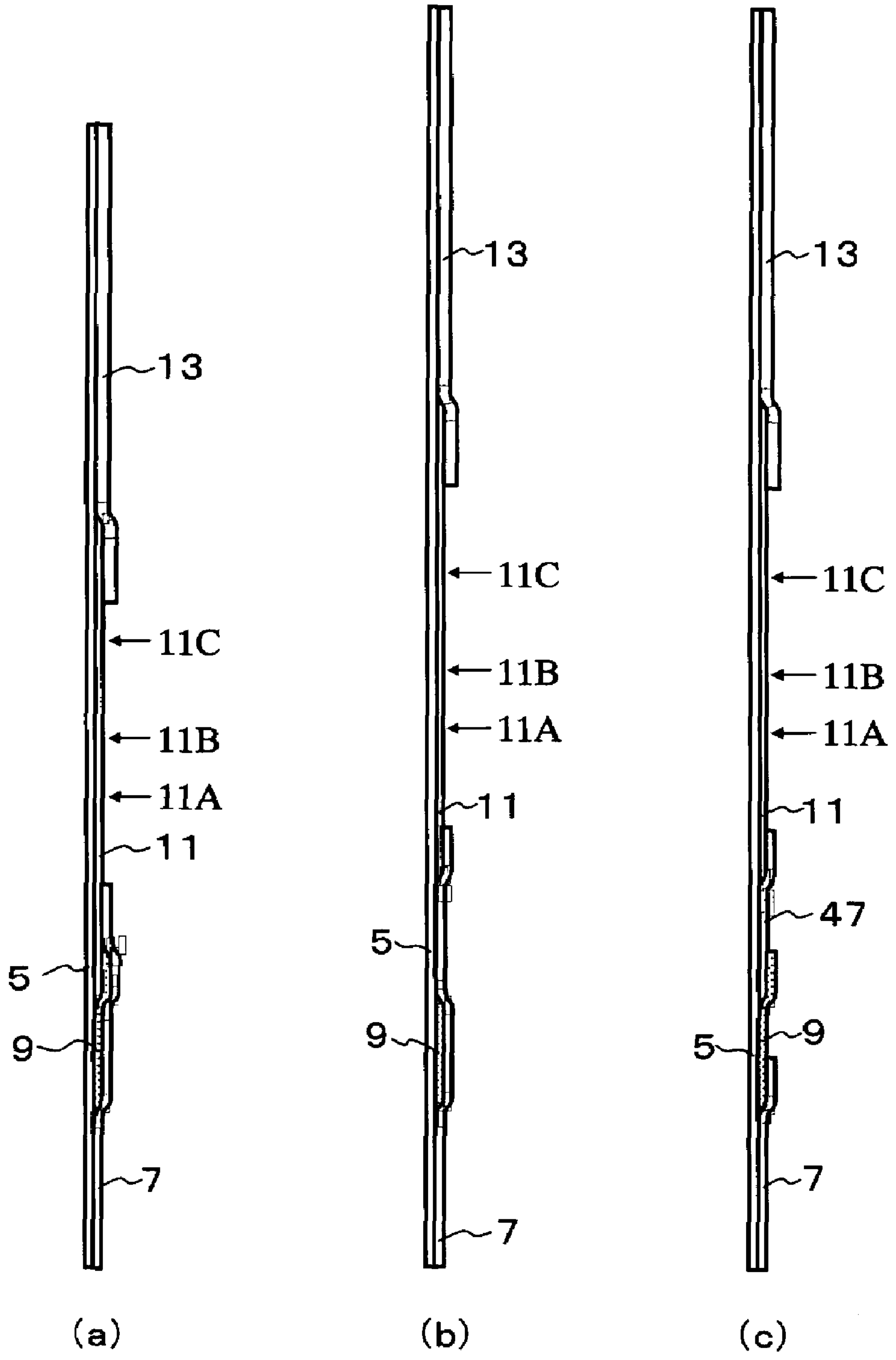

CHROMATOGRAPHY KIT, EXAMINATION CONTAINER, AND METHOD FOR MANUFACTURING THE SAME

FIELD OF THE INVENTION

The present invention relates to a chromatography kit, an examination container used for the chromatography, and a method for manufacturing the same.

BACKGROUND

There is a method to which an chromatographic technique is applied as a manner for assaying simply a variety of diseases by using a body fluid such as blood, blood serum, a laryngeal wiped fluid, a nasal cavity wiped fluid, a nasal discharge, and urine as the specimen material.

The chromatography may be conducted by applying an immunochromatography kit composed of an immunochromatography examination strip for assaying an analyte (pathogenic virus) in a sample, and an examination container which can contain the sample. The examination strip is provided with a sample addition part immersed in the sample, a label holding part for holding a label material for causing an antigen-antibody reaction with respect to the material to be detected in the sample, and a judgment part to which an immobilization material causing an antigen-antibody reaction with respect to the material to be detected is immobilized, these parts being usually disposed on a substrate.

A conventional immunochromatography kit is used commonly in accordance with such a manner that a sample is transferred to an examination container, an examination strip is further inserted in the examination container, thereafter the examination container is disposed in an examination container holder such as a container casing placed on a desk, they are allowed to stand for about 20 minutes, and then, the examination container is taken out from the examination container holder to confirm the presence of lines exhibiting the presence of the material to be detected. During the assay, the sample flows through the sample addition part, the label holding part, and the judgment part in the examination strip.

However, when the substrate of the examination strip inserted in the examination container adheres to the inner wall of the examination container, there is such a case where the sample flows through a gap between the substrate and the examination container due to a capillary phenomenon. As a result, there is a case where an amount of the sample flowing through the sample addition part, the label holding part, and the judgment part decreases, whereby an adequate assay cannot be made. On one hand, when a plane on which the judgment part and the like have been formed adheres on the inner wall of the examination container, there is a case where the assay accuracy decreases.

Furthermore, there is a case where the examination container is inclined or turned over carelessly in case of placing the examination container in the examination container holder, or confirming the presence of the lines. As a consequence, there is a case where the sample in the examination container is flown off, so that the assay result cannot be obtained. In such a case, a body fluid must be collected again from the person being examined; and the reexamination must be conducted. Besides, when such sample is leaked out from the examination container, there is a possibility of the contact between the sample and the assayer.

SUMMARY

The scope of the present invention is defined solely by the appended claims, and is not affected to any degree by the statements within this summary.

An object of the present invention is to provide a chromatography kit which can prevent from adherence of an examination strip on the inner wall of an examination container.

A further object of the present invention is to provide a chromatography kit including an examination container which can prevent from leaking out of the sample contained therein in even a case when the examination container is inclined or turned over.

The chromatography kit of the present invention is provided with an examination container one end of which has an inlet for receiving a sample, and an chromatography examination strip used by inserting from the inlet into the examination container wherein the examination strip includes a sample addition part to be immersed in the sample contained in the examination container, a label holding part for holding a label material causing a reaction with respect to an analyte in the sample, and a judgment part to which an immobilization material causing a reaction with respect to the material to be detected is immobilized; and the examination container includes a prevention part from adherence on an inner wall functioning to prevent from adherence of the examination strip on the inner wall of the examination container.

Since the examination container in the kit of the invention is provided with the prevention part from adherence on an inner wall functioning to prevent from adherence of a member on the inner wall of the examination container, it is possible to prevent from flowing a sample through a gap between a substrate and the examination container due to a capillary phenomenon when an assay is conducted by applying the kit, whereby appropriate and highly accurate assay can be achieved.

The prevention part from adherence on an inner wall to be mounted on the examination container of the present invention is preferably arranged in such that it is disposed on the inner wall or the inlet of the examination container, and it has an oblique plane which comes away from the inner wall of the examination container in the direction of the bottom thereof, whereby a liquid reservoir is formed between the oblique plane and the inner wall of the examination container; the liquid reservoir functioning to retain the sample in case of turning over the examination container. As a result, it is possible to prevent from leaking out of the sample contained in an examination container outside the examination container in even a case when it is erroneously inclined or turned over during conducting an assay by applying the kit.

The prevention part from adherence on an inner wall to be mounted on the examination container of the present invention involves preferably an elongated opening or groove into which the examination strip is to be inserted; and the elongated opening or groove is constituted so as to have such a rotatable range that the examination strip can rotate within a range of ±45° or less, when the examination strip is inserted into the elongated opening or groove. According to the constitution, a freely rotatable range for the examination strip is restricted, so that the orientation of the examination strip is determined at a certain degree. Thus, it becomes possible that an operator observes the assay results from a specified direction.

BRIEF DESCRIPTION OF THE DRAWINGS

FIG. 1 is a view showing a construction of the immunochromatography kit according to an embodiment wherein the prevention part from adherence on an inner wall comprises a member having a smaller throughhole in the opening section than the inlet of the examination container;

FIGS. 2(*a*), 2(*b*), and 2(*c*) are enlarged views wherein FIG. 2(*a*) is a perspective view showing a prevention part from adherence on an inner wall of the examination container in the kit shown in FIG. 1, FIG. 2(*b*) is a top view showing the prevention part of FIG. 2(*a*) viewed from the immediately above direction thereof, and FIG. 2(*c*) is a sectional view taken along the line I-I of FIG. 2(*b*);

FIGS. 3(*a*) and 3(*b*) are top views corresponding to FIG. 2(*b*) wherein FIG. 3(*a*) is a schematic view showing a shape of the prevention part in which a part of a ring is cut off, and FIG. 3(*b*) is another schematic view showing a shape of the prevention part in which a part of another ring is overlapped on another part thereof;

FIGS. 4(*a*), 4(*b*), and 4(*c*) are perspective views each showing a manner for applying the kit shown in FIG. 1;

FIGS. 5(*a*), 5(*b*), and 5(*c*) are a perspective, a top, and a sectional views each showing an embodiment of the prevention part from adherence on an inner wall shown in FIGS. 2(*a*), 2(*b*), and 2(*c*) wherein the section has a columnar contour;

FIGS. 6(*a*), 6(*b*), and 6(*c*) are a perspective, a top, and a sectional views each showing another embodiment of the prevention part from adherence on an inner wall shown in FIGS. 2(*a*), 2(*b*), and 2(*c*) wherein the throughhole has an elongated opening;

FIG. 7 is a perspective view showing another embodiment of the examination container in the kit shown in FIG. 1 wherein the examination container has a quadratic prism contour;

FIGS. 8(*a*) and 8(*b*) are perspective views showing other embodiments of the examination container in the kit shown in FIG. 1 wherein each position of the prevention part from adherence on an inner wall is modified from that of FIG. 1;

FIG. 9 is a perspective view showing a further embodiment of the examination container in the kit shown in FIG. 1 wherein a prevention part from adherence on an inner wall is formed oh the inlet of the examination container;

FIGS. 10(*a*), 10(*b*), and 10(*c*) are enlarged views wherein FIG. 10(*a*) is a perspective view showing a prevention part from adherence on an inner wall of the examination container in the kit shown in FIG. 9, FIG. 10(*b*) is a top view showing the prevention part of FIG. 10(*a*) viewed from the immediately above direction thereof, and FIG. 10(*c*) is a sectional view taken along the line I-I of FIG. 10(*b*);

FIGS. 11(*a*) and 11(*b*) are perspective views each showing a manner for fabricating an examination container by fitting a cylindrical member into another cylindrical member;

FIGS. 12(*a*) and 12(*b*) are perspective views each showing a manner for fabricating an examination container by adhesive bonding a cylindrical member to another cylindrical member;

FIGS. 13(*a*) and 13(*b*) are perspective views each showing a manner for fabricating an examination container by adhesive bonding a cylindrical member which has been divided lengthwise into a half section to another half cylindrical member divided lengthwise;

FIG. 14 is a perspective view showing the immunochromatography kit having the prevention part from adherence on an inner wall which is a guidance part for guiding a sample addition part of the examination strip to the central portion in the bottom of the examination container according to an embodiment of the present invention;

FIG. 15(*a*) is a plan view showing the examination container in the kit shown in FIG. 14, and FIG. 15(*b*) is a sectional view taken along the line I-I of FIG. 15(*a*);

FIG. 16(*a*) is a schematic view showing a working condition of the kit shown in FIG. 14, and FIG. 16(*b*) is a schematic view wherein vicinities of lines 29*a* and 29*b* are viewed in the direction of the arrow X;

FIGS. 17(*a*), 17(*b*), 17(*c*), and 17(*d*) are schematic views each corresponding to the examination container of FIG. 15(*a*) wherein FIGS. 17(*a*), 17(*b*), 17(*c*), and 17(*d*) illustrate a variety of modifications of the examination container;

FIG. 18 is a schematic view corresponding to the examination container of FIG. 15(*b*) wherein FIG. 18 illustrates another embodiment of the examination container;

FIGS. 19(*a*), 19(*b*), and 19(*c*) are schematic views each corresponding to the examination container of FIG. 15(*b*) wherein FIGS. 19(*a*), 19(*b*), and 19(*c*) illustrate a variety of modifications of the examination container;

FIG. 20 is a view showing a constitution of the immunochromatography kit according to an embodiment of the present invention wherein the prevention part from adherence on an inner wall is a projection provided on the inner wall of an examination container;

FIG. 21(*a*) is a plan view showing the examination container in the kit shown in FIG. 20, and FIG. 21(*b*) is a sectional view taken along the line I-I of FIG. 21(*a*);

FIG. 22(*a*) is a schematic view showing a working condition of the kit shown in FIG. 20;

FIGS. 23(*a*) and 23(*b*) are schematic views each showing the examination strips of FIGS. 1, 14 and 20 wherein FIG. 23(*a*) is a side view showing the examination strip, and FIG. 23(*b*) is a front view showing the examination strip; and FIGS. 24(*a*), 24(*b*), and 24(*c*) are schematic views each showing the examination strips of FIGS. 1, 14 and 20 wherein FIGS. 24(*a*), 24(*b*), and 24(*c*) illustrate a variety of modifications of the examination container.

DETAILED DESCRIPTION OF THE PREFERRED EMBODIMENTS

In the following, embodiments of especially an immunochromatography kit regarding the present invention will be described by referring to the accompanying drawings, but it is to be noted that the drawings are used for the explanatory convenience of the invention, and accordingly, the invention is not limited to the embodiments shown in the accompanying drawings.

The immunochromatography kit being an embodiment of the present invention is provided with an examination container one end of which has an inlet for receiving a sample, and an immunochromatography examination strip used by inserting from the inlet into the examination container wherein the examination strip includes a sample addition part to be immersed in the sample contained in the examination container, a label holding part for holding a label material causing an antigen-antibody reaction with respect to an analyte in the sample, and a judgment part to which an immobilization material causing an antigen-antibody reaction with respect to the material to be detected is immobilized; and the examination container includes a prevention part from adherence on an inner wall functioning to prevent from adherence of the examination strip on the inner wall of the examination container.

It is sufficient that the prevention part from adherence on an inner wall may have a function to prevent from adherence of the examination strip on the inner wall of the examination container (more specifically, it is sufficient that the prevention part from adherence on an inner wall has such function that at least a part of the examination strip does not adhere on the inner wall of the examination container, when the examination strip is immersed into a sample contained in the examination container), and accordingly, a variety of manners of practice may be considered.

Under the circumstances, the invention will be described with reference to the following specific manners of practice. Namely, they are (1) the prevention part from adherence on an inner wall comprises a member having a smaller throughhole in the opening section than the inlet of the examination container; (2) the prevention part from adherence on an inner wall is a guidance part for guiding a sample addition part of the examination strip to the central part in the bottom of the examination container; and (3) the prevention part from adherence on an inner wall is a projection provided on the inner wall of the examination container.

In the following, a variety of manners of practice of the examination container will be described first, and a variety of manners of practice of the examination strip will be described finally.

1. A Manner of Practice wherein the Prevention Part from Adherence on an Inner Wall Comprises a Member Having a Smaller Throughhole in the Opening Section than the Inlet of the Examination Container FIG. 1 is a view showing a construction of the immunochromatography kit according to an embodiment wherein the prevention part from adherence on an inner wall comprises the member having a smaller throughhole in the opening section than the inlet of the examination container. The kit is provided with an immunochromatography examination strip 1 for assaying an analyte in a sample, and an examination container 3 capable of containing the sample. The examination container 3 has an inlet 3*a* for receiving the sample at one end thereof and a prevention part from adherence on an inner wall (hereinafter optionally referred simply to as "prevention part") 15 for preventing adherence of an examination strip 1 on an inner wall of the examination container 3. The examination strip 1 is applied by inserting it into the examination container 3 through the inlet 3*a*. The prevention part 15 from adherence on an inner wall comprises a member having a smaller throughhole in the opening section than the inlet of the examination container 3. For the convenience of illustration, the figure of the examination container 3 is the one viewed from the slightly upper direction.

In the present manner of practice, since the prevention part 15 from adherence on an inner wall comprises a member having a smaller throughhole in the opening section than the inlet of the examination container 3, it is possible to prevent from jumping the sample which has been poured into the examination container 3 to the outside in case of turning out of the examination container 3. Accordingly, the prevention part 15 from adherence on an inner wall of the present manner of practice has a function for preventing from leaking-out of the sample. The prevention part 15 is placed at a position under that of a judgment part at the time when the examination strip 1 is inserted in the examination container 3 (i.e. a first judgment part 11A). In this case, the sample is not in contact with the judgment part even if the examination container 3 is turned over. Accordingly, the examination container 3 may be returned to the initial position and the assay may be restarted. It is preferred that the prevention part 15 from adherence on an inner wall is placed at a position under that of a label holding part (i.e. a label holding member 9) at the time when the examination strip 1 is inserted in the examination container 3. In this case, it is possible to prevent from dissolving out the label material maintained in the label holding part into the sample.

FIGS. 2(*a*), 2(*b*), and 2(*c*) are enlarged views wherein FIG. 2(*a*) is a perspective view showing the prevention part 15 from adherence on an inner wall, FIG. 2(*b*) is a top view showing the prevention part of FIG. 2(*a*) viewed from the immediately above direction thereof, and FIG. 2(*c*) is a sectional view taken along the line I-I of FIG. 2(*b*) in which the inside wall 3*c* of the examination container 3 is also indicated by a dotted line according to need.

The prevention part 15 from adherence on an inner wall comprises a ring-shaped member inserted into the examination container 3. The ring-shaped member is made from a resin and the like, and has a certain degree of elasticity, so that it is held at a desired position by means of elastic force. The ring-shaped member may be adhesive bonded to a desired position by means of an adhesive. In place of the ring-shaped member, a member having a shape of the prevention part in which a part of a ring is cut off (see FIG. 3(*a*)), or another member having a shape of the prevention part in which a part of another ring is overlapped on another part thereof (see FIG. 3(*b*)) may also be applied. The members having the shapes as shown in FIGS. 3(*a*) and 3(*b*) are hereinafter referred to as "quasi-ring shaped member". Since the quasi-ring shaped member has a comparatively changeable diameter, it is easily inserted into the examination container 3.

The prevention part 15 from adherence on an inner wall has a throughhole 17 wherein the throughhole 17 is provided with a first opening 17*a* on the side of an inlet 3*a* and a second opening 17*b* on the side of a bottom 3*b*. In the present specification, when the term "opening" is simply used, it is directed to the smaller one in the first and the second openings 17*a* and 17*b*.

The second opening 17*b* is smaller than the first opening 17*a*. The first opening 17*a* has substantially the same size as that of the inlet 3*a* of the examination container 3, while the second opening 17*b* is smaller than the inlet 3*a* of the examination container. Accordingly, the throughhole 17 is tapered off in the direction of the bottom 3*b* of the examination container 3. A side 17*c* of the throughhole 17 forms a slope opened outwardly. The prevention part 15 from adherence on an inner wall forms a truncated cone tapering off in the direction of the bottom 3*b* of the examination container 3 (more specifically, it forms a circular truncated cone). A side 15*a* of the prevention part 15 from adherence on an inner wall is substantially parallel to the side 17*c* of the throughhole 17. In this case, a liquid reservoir portion 19 for retaining a fluid sample in case of turning over the examination container 3 is formed between the side 15*a* of the prevention part 15 from adherence on an inner wall and the inside wall 3*c* of the examination container 3. Hence, it becomes difficult to further leak out the sample outside the examination container in case of turning over the examination container.

Next, a manner for applying an immunochromatography kit of the present embodiment will be described by referring to FIGS. 4(*a*), 4(*b*), and 4(*c*).

First, as shown in FIG. 4(*a*), a specimen material such as a nasal cavity suction fluid of a patient collected by the use of a cotton bud 21 is diluted into a developing solvent 23 contained in a specimen material dilution container 22 to prepare an assay sample 24. Then, a sample transfer pipette 27 is fitted to the specimen material dilution container 22. The sample transfer pipette 27 has a transfer portion 27*a* the sectional contour of which is a substantially circle. However, the sectional contour of the transfer portion 27*a* may have the other contours such as elliptical, quadrangular, and the like shapes.

Next, as shown in FIG. 4(*b*), the transfer portion 27*a* is inserted into the examination container 3, and the side of the specimen material dilution container 22 is pushed, whereby a predetermined amount of the sample 24 is transferred into the examination container 3. Since the throughhole 17 in the prevention part 15 from adherence on an inner wall is tapered off in the direction of the bottom 3*b* of the examination container 3, the sample 24 is guided to the bottom 3*b* of the examination container 3 even when the sample 24 is adhered to the side 17*c* of the throughhole 17.

Then, as shown in FIG. 4(*c*), the examination strip 1 is inserted into the examination container 3. Since the side 17*c* of the throughhole 17 expands in the direction of the inlet 3*a* of the examination container 3, the examination strip 1 can be comparatively easily inserted into the examination container 3. In this condition, when the examination strip 1 and the examination container 3 are allowed to stand for around 10 to 20 minutes, the sample 24 transfers sequentially to a sample addition member 7, a label holding member 9, a chromatography membrane support 11, and an absorption member 13 due to a capillary phenomenon. In the case when the sample 24 passes through the label holding member 9, label materials maintained in the label holding member 9 (a first, a second, and a control label materials) are dissolved out into the developing solvent. When Flu A virus or Flu B virus is contained in the sample, a blue line 29*a* appears in a first judgment part 11A or a second judgment part 11B due to the above-mentioned action. Furthermore, a red line 29*b* appears on a control part 11C irrespective of the presence of a virus (FIG. 4(*c*) shows a case wherein Flu A virus is contained in the specimen material.)

In the following, a variety of embodiments of the prevention part 15 from adherence on an inner wall or the examination container 3 shown in FIG. 1 will be illustrated.

(1) A Columnar Prevention Part from Adherence on an Inner Wall.

The columnar prevention part 15 from adherence on an inner wall is shown in FIGS. 5(*a*) to 5(*c*) wherein FIGS. 5(*a*), 5(*b*), and 5(*c*) correspond to FIGS. 2(*a*), 2(*b*), and 2(*c*), respectively.

The profile of the throughhole 17 in the prevention part 15 from adherence on an inner wall is the same as that of FIGS. 2(*a*), 2(*b*), and 2(*c*), but the outline is in a columnar profile wherein the side 15*a* of the prevention part 15 from adherence on an inner wall is in parallel to the long axial direction of the examination container 3 (the direction in the direction of the inlet 3*a* from the bottom 3*b* of the examination container 3), so that the contact area of the side 15*a* with the inside wall 3*c* of the examination container 3 becomes wider. As a result, the prevention part 15 from adherence on an inner wall of the present embodiment is held stably in the examination container 3.

(2) A Prevention Part from Adherence on an Inner Wall, which has an Elongated Opening.

The prevention part 15 from adherence on an inner wall, which has an elongated second opening 17*b*, is shown in FIGS. 6(*a*), 6(*b*), and 6(*c*) wherein FIGS. 6(*a*), 6(*b*), and 6(*c*) correspond to FIGS. 2(*a*), 2(*b*), and 2(*c*), respectively.

The second opening 17*b* of the throughhole 17 in the prevention part 15 from adherence on an inner wall is formed in an elongated profile (more specifically, a rectangle), but the second opening 17*b* may have an elliptical or the like profile.

When the examination strip 1 is inserted into the second opening 17*b*, the examination strip 1 cannot freely rotate in this condition, so that the rotationally movable range is ±45° or less. The symbol "±" means both the clockwise direction and the counterclockwise direction. In this respect, for example, the expression "±45° or less" means that a rotationally movable range in the clockwise direction is in 45° or less, while the rotationally movable range in the counterclockwise is in 45° or less.

The present embodiment is advantageous in the case where a plurality of the examination containers 3 are aligned in, for example, a rack to assay specimen materials, and the results are confirmed from a certain direction. When the examination strip 1 is freely rotatable, there is such a case where the results cannot be confirmed from the front, because a plane having the judgment part directs transverse or backward directions. In the present embodiment, however, since the rotation angle of the examination strip 1 is in ±45° or less, the assay results can be confirmed from the front thereof so far as the direction of the examination container 3 is appropriately arranged by inserting the examination strip 1 into the examination container 3 having the judgment part in such that the plane thereof is directed to the front thereof.

From the reason as mentioned above, it is desirable that the range wherein the examination strip 1 can rotate has a smaller range, and preferably it is ±30° or less. For reducing a rotationally movable range, it may be arranged in such that a width of the elongated second opening 17*b* is made to be narrowed. On the other hand, when the width is reduced, the sample 24 becomes difficult to pass through the second opening 17*b*. Accordingly, in this respect, it is desirable that the width of the elongated second opening 17*b* has a certain magnitude, so that it is preferred that a rotationally movable range of the examination strip 1 is ±10° or more, and more preferable is around ±20° or more.

Although the examination container 3 may have a columnar profile as shown in FIG. 1, it may have a quadratic prismatic outline (more specifically, a rectangular or a tetragonal prismatic outline) as shown in FIG. 7. A shape of a prevention part 15 from adherence on an inner wall may appropriately be modified so as to correspond to the shape of the examination container 3. A second opening 17*b* has an elongated contour. In this case, when an assay is carried out by such a manner that a plurality of the examination containers 3 are disposed in a rack, the directions of the examination containers 3 may be easily aligned. As a result, it is easily arranged to dispose the examination containers 3 in such that the assay results can be confirmed in the direction from the front thereof in accordance with the present embodiment. In the case where the external profile of the examination container 3 is a quadratic prismatic contour, the internal profile thereof may be a columnar profile.

FIGS. 8(*a*) and 8(*b*) are views each showing an examination container 3 having a modified position of a prevention part 15 from adherence on an inner wall. A position of the prevention part 15 from adherence on an inner wall may be disposed at any position on the examination container 3. In this connection, the prevention part 15 may be positioned in the vicinities at the midpoint of the inlet 3*a* and the bottom 3*b* of the examination container 3 as shown in FIG. 8(*a*), while the prevention part 15 may be positioned in the vicinities of the inlet 3*a* of the examination container 3 as shown in FIG. 8(*b*).

(4) An Examination Container wherein the Prevention Part from Adherence on an Inner Wall is Disposed at the Inlet of the Examination Container The examination container 3 wherein the prevention part 15 from adherence on an inner wall is disposed at the inlet 3*a* of the examination container 3 is shown in FIG. 9. Furthermore, the prevention part 15 from adherence on an inner wall of FIG. 9 is shown in FIGS. 10(*a*), 10(*b*), and 10(*c*) wherein FIGS. 10(*a*), 10(*b*), and 10(*c*) correspond to FIGS. 2(*a*), 2(*b*), and 2(*c*), respectively.

In the present embodiment, the prevention part 15 from adherence on an inner wall is attached to the inlet 3*a* of the examination container 3. In this respect, the prevention part 15 from adherence on an inner wall may be positioned in the vicinities of the inlet 3*a* as shown in FIG. 8(*b*). Since the throughhole 17 is formed vertically in the long axis of the examination container 3, the first opening 17*a* has substantially the same profile as that of the second opening 17*b* wherein the profile of the throughhole 17 may be expanded in the direction of the inlet 3*a* as shown in FIGS. 5(*a*), 5(*b*), and 5(*c*). On one hand, the second opening 17*b* is obtained by combination of the elongated shaped part 31*a* and a reception part 31*b* of the transfer portion 27*a* in the sample transfer pipette 27 shown in FIG. 4(*b*).

The elongated shaped part 31*a* is constituted in such that a rotationally movable range of the examination strip 1 comes to be ±45° or less, when the examination strip 1 is inserted as in the case of the second opening 17*b* having the elongated shape of FIGS. 6(*a*), 6(*b*), and 6(*c*). In the above case, an angle of the rotationally movable range is preferably ±30° C. or less. The reception part 31*b* may have a size by which the transfer portion 27*a* can be received. It is preferred that the reception part 31*b* has substantially the same size as that of the transfer portion 27*a* or a larger size than the transfer portion 27*a*. More preferable is that the reception part 31*b* has an analogous profile to that of the transfer portion 27*a*.

In the case where the second opening 17*b* has the elongated shape as shown in FIG. 6, there is an event wherein the sample 24 is difficult to pass through the throughhole 17 since a width of the opening is narrow. In the present embodiment, however, the sample 24 can be transferred under the condition wherein the transfer portion 27*a* is thrust into the throughhole 17, so that no problem arises with respect to the matter as described above.

In the embodiments which have been mentioned so far, although the prevention part 15 from adherent on an inner wall is formed by providing a ring-shaped member on the examination container 3, the prevention part 15 from adherent on an inner wall may also be formed in accordance with the manners as described hereunder.

(1) Fabrication of an Examination Container by Connecting Two Cylindrical Members with Each Other The examination container 3 is fabricated by such a manner that a throughhole cylindrical member 35*a* containing the prevention part 15 from adherence on an inner wall at an end 33 thereof and a cylindrical member 35*b* with a bottom capable of containing a sample are prepared as shown in FIG. 11(*a*); and the cylindrical member 35*b* with a bottom is fitted to the end 33 of the throughhole cylindrical member 35*a* to connect them to each other as shown in FIG. 11(*b*). In the present embodiment, the end 33 is preferably tapered off in view of being easily fitted. Although the illustration of the embodiment has been made with an example wherein the examination container 3 similar to that of FIG. 1 is shown, the manner of practice may be applied essentially to any of the embodiments which have been mentioned so far.

In another embodiment, an examination container 3 is fabricated by such a manner that a throughhole cylindrical member 35*a* having a bonding surface 33*a* at an end 33 thereof on which a prevention part 15 from adherence on an inner wall is provided and a cylindrical member 35*a* with a bottom having a bonding surface 33*b* and capable of containing a sample are prepared as shown in FIG. 12(*a*); and these bonding surfaces 33*a* and 33*b* are bonded to each other to connect the cylindrical member 35*b* with the bottom is connected to the end 33 of the throughhole cylindrical member 35*a* as shown in FIG. 12(*b*).

(2) Fabrication of an Examination Container by Bonding Two Vertically Divided Members The examination container 3 is fabricated by such a manner that a pair of structural members 37 each having a constitution obtained by dividing the examination container 3 having a prevention part 15 from adherence on an inner wall by a longitudinal section passing through the center of the examination container 3 are prepared as shown in FIG. 13(*a*); and these structural members 37 are bonded to each other as shown in FIG. 13(*b*) wherein a trace 39 of the bonding exists in the fabricated examination container 3.

The above-described manner of practice may be applied essentially to any of the embodiments which have been mentioned so far. It is preferred, however, that the prevention part 15 from adherence on an inner wall has a columnar profile as shown in FIGS. 5(*a*), 5(*b*), and 5(*c*). The structural members 37 may be molded by means of injection molding. In this case, if the prevention part 15 from adherent on an inner wall has a columnar profile, the structural member 37 can be easily taken out from a metal mold.

2. A Manner of Practice wherein the Prevention Part from Adherence on an Inner Wall which is a Guidance Part for Guiding a Sample Addition Part of the Examination Strip to the Central Portion in the Bottom of the Examination Container.

FIG. 14 is a perspective view showing an embodiment of the immunochromatography kit according to the present invention wherein a guidance part for guiding a sample addition part of the examination strip to the central portion in the bottom of the examination container is provided as a prevention part from adherence on an inner wall. The kit comprises an immunochromatography examination strip 1 for assaying an analyte in a sample, and an examination container 40 for containing the sample. The examination container 40 has an inlet 40*a* for receiving the sample at an end thereof. The examination strip 1 is used by inserting it into the examination container 40 through the inlet 40*a*. The drawing of the examination container 40 is illustrated from the slightly upper direction thereof for the convenience of the illustration.

For the explanation, the examination container 40 of FIG. 14 is shown in a plan view of FIG. 15(*a*), and a sectional view taken along the line I-I of FIG. 15(*a*) is shown in FIG. 15(*b*). The examination container 40 is provided with a prevention part 41 from adherence on an inner wall functioning as a guidance part for guiding a sample addition member 7 of the examination strip 1 to a central portion 40*b* in the bottom of the examination container 40. The examination container 40 has a quadratic prismatic profile. The prevention part 41 from adherence on an inner wall has a tapered surface 41*a* directing from an inner wall 40*c* of the examination container 40 to the central portion 40*b* of the bottom in the examination container 40. The tapered surface 41*a* is inclined so as to approach to the bottom of the examination container 40 with backing away from the inner wall 40*c* of the examination container 40. The prevention part 41 from adherence on an inner wall is provided with a slit 41*b* for receiving the sample addition member 7 in the central portion 40*b* of the bottom of the examination container 40. The slit 41*b* is formed as shown in the plan view of FIG. 15(*a*) in such that the direction of the slit 41*b* comes to be in parallel to at least one side of the inner wall 40*c* of the examination container 40. The slit 41*b* comprises two sides 41*c* wherein these sides 41*c* are substantially parallel to each other; and the respective sides 41*c* are substantially perpendicular to the bottom of the examination container 40.

The slit 41*b* functions to make the examination strip 1 to be away from the inner wall 40*c* of the examination container and at the same time, functions to restrict a range wherein the examination strip 1 is freely rotatable in the examination container 40 to determine a direction of the examination strip 1 at a certain degree. Accordingly, it is desirable that a width of the slit 41*b* is not excessively broad, so that the width as to a rotationally movable range of the examination strip 1 is ±45° or less (preferably it is around ±40° or less, and more preferably it is around ±30° or less).

The prevention part 41 from adherence on an inner wall may be molded monolithically with the examination container 40 by means of injection molding and the like. On one hand, the prevention part 41 may be formed by inserting a separate member into the examination container 40 to fix the separate member to the bottom of the examination container 40. The examination container 40 and the prevention part 41 from adherence on an inner wall may be made from a resin, glass and the like.

Next, one example of a method for applying the kit of the present embodiment will be described by referring to FIG. 16(*a*).

First, a plurality of the examination containers 40 is aligned in a rack or the like. In this case, the examination containers 40 are positioned so as to direct each of the slits 41*b* thereof to the same direction to each other. Then, a predetermined amount of a sample 24 prepared by diluting a nasal cavity suction fluid of a patient into a developing solvent is transferred in the examination container 40. Thereafter, the examination strip 1 is inserted into the examination container 40. The sample addition member 7 of the examination strip 1 is guided to the central portion 40*b* of the bottom in the examination container 40 by means of the tapered surface 41*a* of the prevention part 41 from adherence on an inner wall, and finally it is contained in the slit 41*b*.

Under the condition, when the examination container 40 and the examination strip 1 are allowed to stand for around 10 to 20 minutes, the sample 24 transfers sequentially from the sample addition member 7 to the label holding member 9, the chromatography membrane support 11, and the absorption member 13 due to a capillary phenomenon. In the case when the sample 24 passes through the label holding member 9, label materials maintained in the label holding member 9 (a first, a second, and a control label materials) are dissolved out into the developing solvent. When Flu A virus or Flu B virus is contained in the sample, a blue line 29*a* appears in a first judgment part 11A or a second judgment part 11B due to the above-mentioned action. Furthermore, a red line 29*b* appears on a control part 11C irrespective of the presence of a virus (FIG. 16(*a*) shows a case wherein Flu A virus is contained in the specimen material.) For reference, a schematic diagram indicating the vicinities of the lines 29*a* and 29*b* viewed from the direction of the arrow X is shown in FIG. 16(*b*).

When the kit of the present embodiment is applied, the sample addition member 7 of the examination strip 1 is contained in the slit 41*b*. Thus, the examination strip 1 comes inevitably away from the inner wall 40*c* of the examination container 40. As a result, adherence of the examination strip 1 on the inner wall 40*c* of the examination container 40 is prevented. Furthermore, since the slit 41*b* is formed so as to extend in parallel to the inner wall 40*c* of the examination container 40 as appeared in the plan view of FIG. 15(*a*), a plane onto which the chromatography membrane support 11 and the like of the examination strip 1 are fixed directs to the direction of the arrow X. As mentioned herein, the direction of the examination strip 1 is determined by the slit 41*b* at a certain degree. Accordingly, when the directions of the slits 41*b* are aligned in case of setting up examination containers 40 in a rack, the directions of the examination strips 1 inserted in the respective examination containers 40 can be aligned. Thus, in the case where a plurality of the examination containers 40 are applied to conduct the assay with respect to a plurality of specimen materials, the results thereof can be observed from a certain direction in accordance with the present embodiment.

The profile of the examination container 40 is not limited to the quadrangle in the plan view as shown in FIG. 15(*a*), but the other profiles are also applicable. A variety of embodiments of the examination container 40 are shown in the plan views of FIGS. 17(*a*), 17(*b*), 17(*c*), and 17(*d*) wherein the circular shape of the plan view as shown in FIG. 17(*a*) is applicable, the shape in which a side of the inner wall is rounded adjacent to the slit 41*b* of the plan view as shown in FIG. 17(*b*) is applicable, the shape in which a side of the inner wall adjacent to the slit 41*b* is made to be narrower than that of the other inner wall of the plan view as shown in FIG. 17(*c*) is applicable, and the hexagonal shape of the plan view as shown in FIG. 17(*d*) is applicable. In the shape of FIG. 17(*c*), it is preferred that the width of the narrower inner wall is narrower than that of the examination strip 1. This is because the examination strip 1 becomes further difficult to adhere on the inner wall. Likewise, it is preferred in the shape of FIG. 17(*d*) that the width of the inner wall in parallel to the slit 41*b* is narrower than that of the examination strip 1.

Moreover, as shown in FIG. 18, at least one side wall of the examination container 40 may have a curved surface expanded in the direction wherein the volume of the examination container 40 increases. Because of such arrangement as described above, the examination strip 1 becomes further difficult to adhere on the inner wall 40*c* of the examination container 40.

The outline of the prevention part 41 from adherence on an inner wall is not limited to that shown in FIG. 15(*b*), but the other outlines may also be applied. A variety of embodiments of the examination container 40 having a different profile of the prevention part 41 from adherent on an inner wall is shown in FIGS. 19(*a*), 19(*b*), and 19(*c*) wherein FIG. 19(*a*) shows an example in which a side 41*c* of a slit 41*b* in the prevention part 41 from adherent on an inner wall is not perpendicular to the bottom of the examination container 40. In FIG. 19(*a*), the slit 41*b* is constituted by a slit side surface 41*c* having a larger angle than that of a tapered surface 41*a* with respect to the bottom of the examination container 40. In FIG. 19(*b*), the prevention part 41 from adherent on an inner wall is not provided with the slit 41*b*. In even this case, the prevention part 41 from adherent on an inner wall has a function to guide the sample addition member 7 of the examination strip 1 to the central portion 40*b* of the bottom in the examination container. In FIG. 19(*c*), the bottom of the examination container 40 is to be peaked.

3. A Manner of Practice wherein the Prevention Part from Adherence on an Inner Wall is a Projection Provided on the Inner Wall of the Examination Container.

FIG. 20 is a view showing the immunochromatography kit according to an embodiment of the invention wherein the prevention part from adherence on an inner wall is a projection provided on the inner wall of an examination container. The kit is provided with an immunochromatography examination strip 1 for detecting a substance to be detected in a sample, and an examination container 43 capable of containing the sample. The examination container 43 involves an inlet 43*a* for receiving the sample at one end thereof. The examination strip 1 is used by inserting into the examination container 43 through the inlet 43*a*. The examination container 43 is illustrated in the drawing in such a manner that it is shown from the position where is a slightly upper position than the real position for the convenience of the illustration and easy understanding.

For the explanation, FIG. 21(*a*) shows a plan view of the examination container 43 illustrated in the FIG. 20, while FIG. 21(*b*) is a sectional view taken along the line I-I of FIG. 21(*a*).

The examination container 43 is provided with a prevention part 45 from adherence on an inner wall, which comprises a projection provided on an inner wall 43*b* of the examination container 43. The projection forms a space between the examination strip 1 and the inner wall 43*b* of the examination container 43, whereby the adherence of the examination strip 1 on the inner wall 43*b* of the examination container 43 is prevented.

The examination container 43 has a rectangular prismatic shape, so that when the examination strip 1 is inserted into the examination container 43, the examination strip 1 does not rotate freely inside the examination container 43, whereby the orientation thereof is determined at a certain degree to be opposed to a specified inner wall of the examination container 43. It is preferred that the examination container 43 has a shape based on which a rotatable range of the examination strip 1 is to be within a range of ±45° or less (preferably ±40° or less, and more preferably ±30° or less).

In one example, X is 5 mm, Y is 8 mm, and a wall thickness is 1 mm in the examination container 43.

Since the prevention part 45 from adherence on an inner wall is provided for preventing the adherence of the examination strip 1 on the inner wall 43*b* of the examination container 43, the prevention part 45 is provided on the inner wall 43*b* where there is a possibility of the contact of the inner wall 43*b* with the front or the back of the examination strip 1. In other words, since there is a possibility of contact of the front (on which a judgment part or the like is formed) or the back (on which the substrate 5 is exposed) of the examination strip 1 with a pair of inner walls 43*b* (the pair of the inner walls perpendicular to the drawing) having a wider area than that of the other pair of inner walls (the pair of the inner walls parallel to the drawing) in the two pairs of inner walls wherein each pair of the inner walls is opposed to each other (the pair of the inner walls parallel to the inner wall, and the other pair of the inner walls perpendicular to the drawing), one each of the prevention part 45 from adherence on the inner wall is disposed on the pair of the inner walls 43*b*. The prevention part 45 is disposed in the vicinities of the central portion of the inner wall 43*b*. The prevention part 45 from adherence on the inner wall has a conical outline the extreme end of which is rounded.

In one example, the prevention part 45 from adherence on the inner wall is projected by 1 mm from the inner wall, and a diameter of the widest part of cone is 3 mm.

The prevention part 45 may be integrally molded with the examination container 43 by means of injection molding and the like, or the prevention part 45 may be formed also by fixing a separate member onto the examination container 43. Furthermore, the prevention part 45 may be formed by making the wall of the examination container 43 to hollow inwards. The examination container 43 and the prevention part 45 from adherence on an inner wall may be manufactured from a resin, glass or the like. The same or different materials may be applied for the examination container 43 and the prevention part 45 from adherence on an inner wall.

Next, one example of a method for applying the kit of the present embodiment will be described by referring to FIG. 22.

First, a predetermined amount of a sample 24 prepared by diluting a nasal cavity suction fluid of a patient into a developing solvent is transferred in the examination container 43. Then, the examination strip 1 is inserted into the examination container 43.

Under the condition, when the examination container 40 and the examination strip 1 are allowed to stand for around 10 to 20 minutes, the sample 24 transfers sequentially from the sample addition member 7 to the label holding member 9, the chromatography membrane support 11, and the absorption member 13 due to a capillary phenomenon and the sample is examined.

There is a possibility of appearance of such a problem that assay precision decreases and the like, when the front or the back of the examination strip 1 adheres on the inner wall 43*b* of the examination container 43. In the present manner of practice, however, since the prevention part 45 from adherence on an inner wall is provided on the inner wall 43*b* of the examination container 43, the substrate 5 of the examination strip 1 does not adhere on the inner wall 43*b* of the examination container 43 as shown in FIG. 22, and thus, there is no problem as described above.

Although the invention has been described so far with taking the specified manners of practice as examples, the present invention is not limited to the manners of practice, but a variety of modifications is applicable.

An outline of the examination container 43 is not limited to a rectangular prismatic shape, but it may be the other shapes, for example, it may be a tetragonal prismatic shape. In this case, there is such a possibility that the front or the back of the examination strip 1 comes to be in contact with all the four inner walls of the examination container 43, so that it is preferred to provide the prevention part 45 from adherence on an inner wall on each of the four inner walls. The prevention part 45 may be provided on all the inner walls where the front or the back of the examination strip 1 comes to be in contact with the examiner container 43. However, the prevention part 45 may be provided on only the inner wall of the examination strip 1 with which there is such a possibility that the front of the examination strip 1 comes to be in contact, or only the inner wall of the examination strip 1 with which there is such a possibility that the back of the examination strip 1 comes to be in contact.

The number of the prevention part 45 from adherent on an inner wall is not specifically restricted, but it may be only one, or two or more. The position at which the prevention part 45 from adherent on an inner wall is to be disposed is not limited, for instance, it may be a position near to the bottom of the examination container 43, or that near to the inlet of the examination container 43.

A shape of the prevention part 45 from adherence on an inner wall is not specifically restricted, but it may be any of a hemispherical, columnar, polyhedron prismatic, polyhedral, and the like shapes wherein the extreme end of the prevention part 45 from adherence on an inner wall may be sharpened or rounded.

4. Explanation of an Examination Strip.

FIGS. 23(*a*) and 23(*b*) are a side view and a front view showing the examination strip 1 of FIGS. 1, 14 and 20 wherein the examination strip 1 comprises a substrate 5 made of a plastic sheet having an adhesive layer on the surface thereof on which a sample addition member 7 made of a rayon non-woven fabric, a label holding member 9 made of a glass fiber non-woven fabric, a chromatography membrane support 11 made of a nitrocellulose porous member, and an absorption member 13 made of a cellulose non-woven fabric are provided. The sample addition member 7 functions as a sample addition part to be immersed in a sample contained in the examination container 3. The label holding member 9 is disposed in contact with the sample addition member 7 and functions as a label holding part for holding a label material causing an antigen-antibody reaction with an analyte in the sample. The chromatography membrane support 11 is disposed in contact with the label holding member 9 and has a judgment part to which an immobilization material causing an antigen-antibody reaction with respect to the material to be detected is immobilized. The absorption member 13 is disposed so as to be in contact with the chromatography membrane support 11.

On the chromatography membrane support 11, a line-like first judgment part 11A, a second judgment part 11B, and a control part 11C are formed in this order from the upstream side thereof. In the label holding member 9, the first label material, the second label material, and the control label material are maintained. In the first judgment part 11A, the second judgment part 11B, and the control part 11C, anti-influenza A antibody and anti-influenza B antibody (hereinafter referred to as "anti Flu A antibody" and "anti Flu B antibody", respectively), and biotin are immobilized, respectively, as an immobilization material. Furthermore, indications "A", "B", and "!" indicating the classifications thereof, respectively, are printed at the positions corresponding to the first judgment part 11A, the second judgment part 11B, and the control part 11C, respectively. The first label material and the second label material are the anti Flu A antibody and the anti Flu B antibody labeled with blue latex particles, respectively. The control label material is avidin labeled with red latex particles. The anti Flu A antibody and the anti Flu B antibody are combined with influenza A type virus which is a first material to be detected and influenza B type virus which is a second material to be detected (hereinafter referred to as "Flu A virus" and "Flu B virus", respectively) through an antigen-antibody reaction.

Taking Flu A virus as an example, the anti Flu A antibody labeled and existing in the label holding member 9 recognizes a predetermined site of the Flu A virus to form a compound material as a result of the combination through an antigen-antibody reaction, when the Flu A virus is contained in a sample. Then, the anti Flu A antibody existing in the chromatography membrane support 11 recognizes the other site of the Flu A virus to capture the compound material. When the compound material is captured, a blue line appears on the first judgment part 11A, whereby the Flu A virus is detected by visual observation.

In addition, although avidin is not captured by the anti Flu A antibody and the anti Flu B antibody existing in the chromatography membrane support 11, it is captured by the biotin immobilized in the control part 11C, because it combines specifically with biotin. When the avidin is captured, a red line appears on the control part 11C, whereby it is visually observed that the avidin reaches the control part 11C. Since the control part 11C is positioned on the downstream side of the first judgment part 11A and the second judgment part 11B, when the red line is confirmed, it is confirmed that the sample passes through the first judgment part 11A and the second judgment part 11B.

Next, a variety of embodiments of the examination strips 1 will be described. The examination strip 1 may be those shown in FIGS. 24(*a*), 24(*b*), and 24(*c*) other than that shown in FIGS. 23(*a*) and 23(*b*). In the examination strip shown in FIG. 24(*a*), the strip is constituted in such that a sample addition member 7 covers a label holding member 9 to be contact with the chromatography membrane support 11. In the examination strip shown in FIG. 24(*b*), it is constituted in such that the label holding member 9 is disposed so as to keep a gap with respect to the chromatography membrane support 11, and the sample addition member 7 covers the label holding member 9 so as to be in contact with the chromatography membrane support 11. In the examination strip shown in FIG. 24(*c*), it is constituted in such that the label holding member 9 is disposed so as to keep a gap with respect to the chromatography membrane support 11, and a developing member 47 is disposed so as to be in contact with the label holding member 9 and the chromatography membrane support 11. The developing member 47 may be prepared by a non-woven fabric made from a variety of raw materials such as rayon, glass fiber, cellulose fibers and the like as in the case of the sample addition member 7. According to the constitutions shown in FIGS. 24(*b*) and 24(*c*), since a member which exhibits a rapid developing rate of a sample is sandwiched between the label holding member 9 and the chromatography membrane support 11, a rate of dissolving out the label material in the label holding member 9 becomes fast, so that a rapid measurement becomes possible.

Although the invention has been described so far with taking the specified manners of practice as examples, the present invention is not limited to the manners of practice, but a variety of modifications is applicable.

The prevention part from adherence on an inner wall in the present invention means a mechanism for preventing from adherence of the examination strip on the inner wall of the examination container. Particularly, it is preferred that the prevention part from adherence on the inner wall is located so as to form a space by which the judgment part of the examination strip does not adhere on the inner wall of the examination container, when the examination strip is inserted into the examination container. Besides, when the prevention part from adherence on the inner wall is provided with a liquid reservoir for retaining a fluid sample at the time of turning over the examination container, it is possible to prevent from leaking out of the sample outside the examination container.

An analyte which is applied in the present invention is not specifically restricted so far as a material is the one which causes an antigen-antibody reaction. An example of such materials as described above includes cells of bacteria, protist, fungi and the like; viruses, proteins, polysaccharides and the like. For instance, there are parainfluenza viruses, RS viruses, *Mycoplasma pneumoniae*, rotaviruses, caliciviruses, coronaviruses, adenoviruses, enteroviruses, herpesviruses, human immunodeficiency viruses, hepatitis viruses, disease viruses of severe acute respiratory syndrome other than the above-described influenza viruses; *Bacillus coli, Staphylococcus aureus, Streptococcus pneumoniae, Streptococcus piyogenes*; malaria parasite, and the other causal organisms of various diseases such as alimentary diseases, central nervous system diseases, and hemorrhagic fever; the metabolic products thereof; carcinoembryonic antigens; tumor markers such as Cyfra; hormones and the like.

The substrate 5 is a material for disposing appropriately the above-described members such as the sample addition member 7, and label holding member 9; and it may be prepared from a variety of materials such as papers, and glass in addition to plastics. Furthermore, the sample addition member 7 may be prepared from a variety of raw materials such as glass fibers, and cellulose fibers in addition to rayon. The label holding member 9 may be prepared from a variety of materials such as cellulose fibers in addition to glass fibers. The chromatography membrane support 11 may be prepared from a variety of materials such as nylon (for example, a modified nylon into which an amino group that may have a carboxyl group or an alkyl group as a substituent is introduced), polyvinylidenedifluoride (PVDF), and cellulose acetates in addition to nitrocellulose. The absorption member 13 may be prepared from a variety of materials such as glass fibers in addition to celluloses. For the sample addition member 7, the label holding member 9, the chromatography membrane support 11, and the absorption member 13, materials each having a variety of structures wherein a sample can be developed due to a capillary phenomenon may be applied in addition to non-woven fabrics and porous materials.

The chromatography membrane support 11 may be provided with either one judgment part, or two or more judgment parts in response to types of materials to be detected. Further, the chromatography membrane support 11 may be provided with no control part. In this connection, the judgment parts and the control part may not be in a line-like shape, but they may be formed into, for example, a circular, a square or the like shape. The label holding member 9 may maintain only one label material or two or more label materials. Furthermore, the label holding material 9 may be provided with no control label material. The label material is labeled with latex particles with a color other than blue and red; a metal colloid of gold or the like; or dye/pigment molecules and the like. In the case where there are two or more types of label materials, each label material may be labeled in different colors from one another, or in the same color. Moreover, the label materials and the control label materials may be labeled in different colors from one another, or in the same color.

In the above-described embodiments, although the classification indications of the first judgment part 11A, the second judgment part 11B, and the control part 11C are printed on the chromatography membrane support 11, these classification indications may be applied by a manner other than the printing, or may not be applied. The above-described classification indications may be applied on the examination container 3 at the positions corresponding to the first judgment part 11A, the second judgment part 11B, and the control part 11C, when the examination strip 1 is inserted in the examination container 3. In addition, the classification indications may be applied with the symbols other than that of "A", "B", and "!".

For the immobilization materials and the label materials, a variety of antibodies and antigens may be applied. Namely, in the case where an analyte is an antigen, an antibody which causes an antigen-antibody reaction with the antigen may be used as the immobilization material and the label materials, while in the case where an analyte is an antibody, an antigen which causes an antigen-antibody reaction with the antibody or the antibody being the material to be detected which causes an antigen-antibody reaction with the antibody may be used as the immobilization material and the label materials.

The immobilization material of the control part may be avidin, and the control label material may be biotin. Moreover, the immobilization material of the control part and the control label material are those of materials other than that of a combination of biotin and avidin. For instance, it may be a combination of materials combined through an antigen-antibody reaction. For example, an antigen is used as the control label material, while an antibody which causes an antigen-antibody reaction with the antigen as an immobilization material of the control part is used; and vice versa. For the control label material, those which cause no antigen-antibody reaction with an analyte or an immobilization material in the judgment part are applied.

A variety of characteristics described in the above manners of practice may be combined with each other. In the case where a plurality of characteristics is contained in a manner of practice, one or plural characteristics thereof may be appropriately taken out, and they may be used alone or in combination thereof in order to apply them for the kit according to the present invention.

The foregoing detailed description and accompanying drawings have been provided by way of explanation and illustration, and are not intended to limit the scope of the appended claims. Many variations in the presently preferred embodiments illustrated herein will be obvious to one on ordinary skill in the art, and remain within the scope of the appended claims and their equivalents.

What is claimed is:

1. A chromatography kit, comprising:

an examination container comprising an elongated and bottomed container body having an inlet at one end for receiving a sample, and a chromatography examination strip used by inserting from the inlet into the examination container;

wherein the examination container comprises a prevention part for preventing the adherence of the examination strip on the inner wall of the examination container;

wherein the prevention part has a throughhole having an elongated shape and disposed between the inlet and the bottom of the container body;

wherein the throughhole of the prevention part is smaller than the inlet of the container body;

wherein the throughhole of the prevention part restricts a rotationally movable range of the examination strip so as to be ±45° or less when the examination strip is inserted into the throughhole; and wherein the examination container is a capless container not having a cap placed on the inlet.

2. The kit as claimed in claim 1, wherein:

the examination strip comprises a sample addition part to be immersed into the sample contained in the examination container, a label holding part for holding a label material binding to an analyte in the sample, and a judgment part to which an immobilization material binding to an analyte is immobilized.

3. The kit as claimed in claim 1, wherein:

the throughhole is tapered off in the direction of the bottom of the examination container.

4. The kit as claimed in claim 1, wherein:

the prevention part has a frustum-shaped throughhole in which the hole is tapered off in the direction of the bottom of the examination container.

5. The kit as claimed in claim 4, wherein:

the prevention part is constituted so as to form a liquid reservoir for retaining the sample between a frustum-shaped oblique plane of the prevention part and the inner wall of the examination container, when the examination container is turned over.

6. The kit as claimed in claim 1, wherein:

the prevention part comprises a ring-shaped member or a quasi-ring shaped member.

7. The kit as claimed in claim 1, wherein:

the examination container comprises a throughhole cylindrical member forming the prevention part at an end thereof; and a cylindrical member having a bottom and connected to the end of the throughhole cylindrical member in which the sample can be contained.

* * * * *

UNITED STATES PATENT AND TRADEMARK OFFICE
CERTIFICATE OF CORRECTION

PATENT NO. : 7,642,087 B2
APPLICATION NO. : 11/527562
DATED : January 5, 2010
INVENTOR(S) : Takeshi Imoarai et al.

It is certified that error appears in the above-identified patent and that said Letters Patent is hereby corrected as shown below:

Delete Title page showing an illustrative figure and substitute the attached Title page therefor.

Delete drawing figures 1-12 and 14-24 and replace the drawings with the substitute drawings filed herewith.

Signed and Sealed this

Third Day of August, 2010

David J. Kappos

David J. Kappos
*Director of the United States Patent and Trademark Office*

(12) United States Patent
Imoarai et al.

(10) Patent No.: US 7,642,087 B2
(45) Date of Patent: Jan. 5, 2010

(54) CHROMATOGRAPHY KIT, EXAMINATION CONTAINER, AND METHOD FOR MANUFACTURING THE SAME

(75) Inventors: Takeshi Imoarai, Kobe (JP); Shinya Nagai, Akashi (JP); Motoi Furutani, Akashi (JP); Kanako Horisaka, Akashi (JP)

(73) Assignee: Sysmex Corporation, Hyogo (JP)

( * ) Notice: Subject to any disclaimer, the term of this patent is extended or adjusted under 35 U.S.C. 154(b) by 228 days.

(21) Appl. No.: 11/527,562

(22) Filed: Sep. 27, 2006

(65) Prior Publication Data

US 2007/0178606 A1 Aug. 2, 2007

(30) Foreign Application Priority Data

Sep. 27, 2005 (JP) ............................ 2005-280587
Sep. 28, 2005 (JP) ............................ 2005-282399
Jul. 28, 2006 (JP) ............................ 2006-206619

(51) Int. Cl.
*C12M 1/34* (2006.01)
*C12M 3/00* (2006.01)

(52) U.S. Cl. ................ 435/287.2; 435/287.1; 435/970; 435/973; 435/875; 436/518; 436/514; 422/56; 422/57; 422/58; 422/59; 422/60; 422/61; 422/68.1; 422/102

(58) Field of Classification Search ............ 422/56 61, 422/68.1, 102; 435/287.1, 970, 287.2, 973, 435/875
See application file for complete search history.

(56) References Cited

U.S. PATENT DOCUMENTS 3,776,220 A * 12/1973 Monaghan .................. 600/572
4,387,725 A * 6/1983 Mull .......................... 600/572
5,712,172 A 1/1998 Huang et al.
6,403,383 B1 * 6/2002 Casterlin et al. ........... 436/518
6,461,873 B1 * 10/2002 Catania et al. ............. 436/518
6,537,828 B1 3/2003 Nakaya et al.
2003/0190745 A1 * 10/2003 Galloway et al. ........ 435/287.2

* cited by examiner

*Primary Examiner*—Bao-Thuy L Nguyen
(74) *Attorney, Agent, or Firm*—Sughrue Mion, PLLC

(57) ABSTRACT

An chromatography kit is described, a representative one of which includes: an examination container one end of which has an inlet for receiving a sample, and an chromatography examination strip used by inserting from the inlet into the examination container wherein the examination container comprises a prevention part for preventing from the adherence of the examination strip on the inner wall of the examination container.

7 Claims, 21 Drawing Sheets

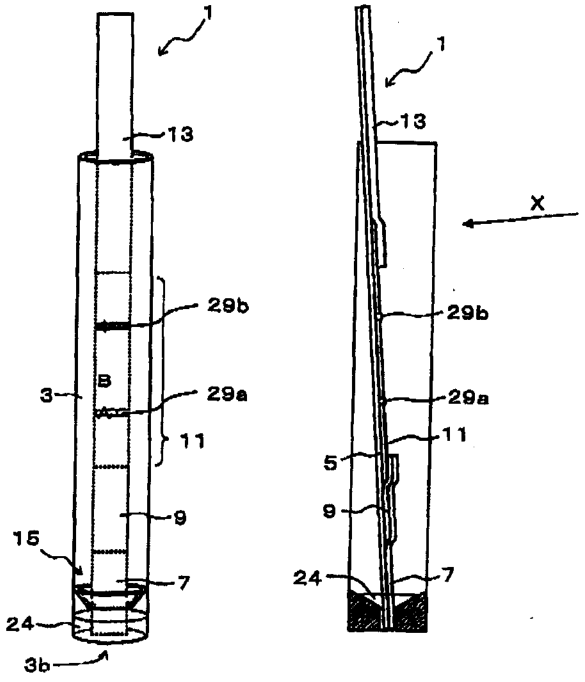

[Fig. 1]
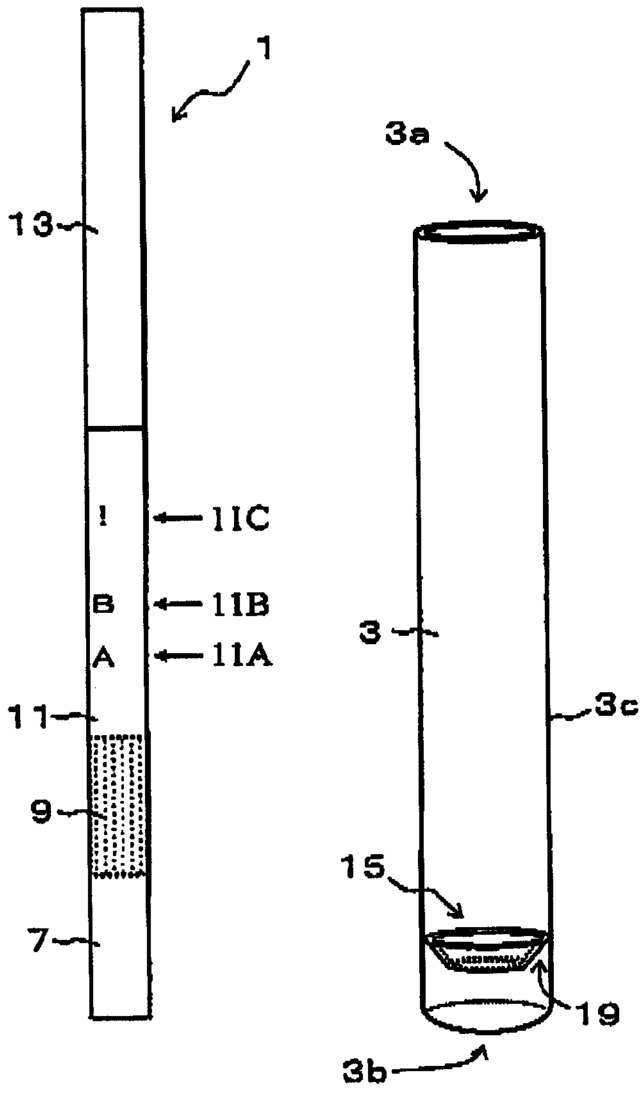

[Fig. 2]
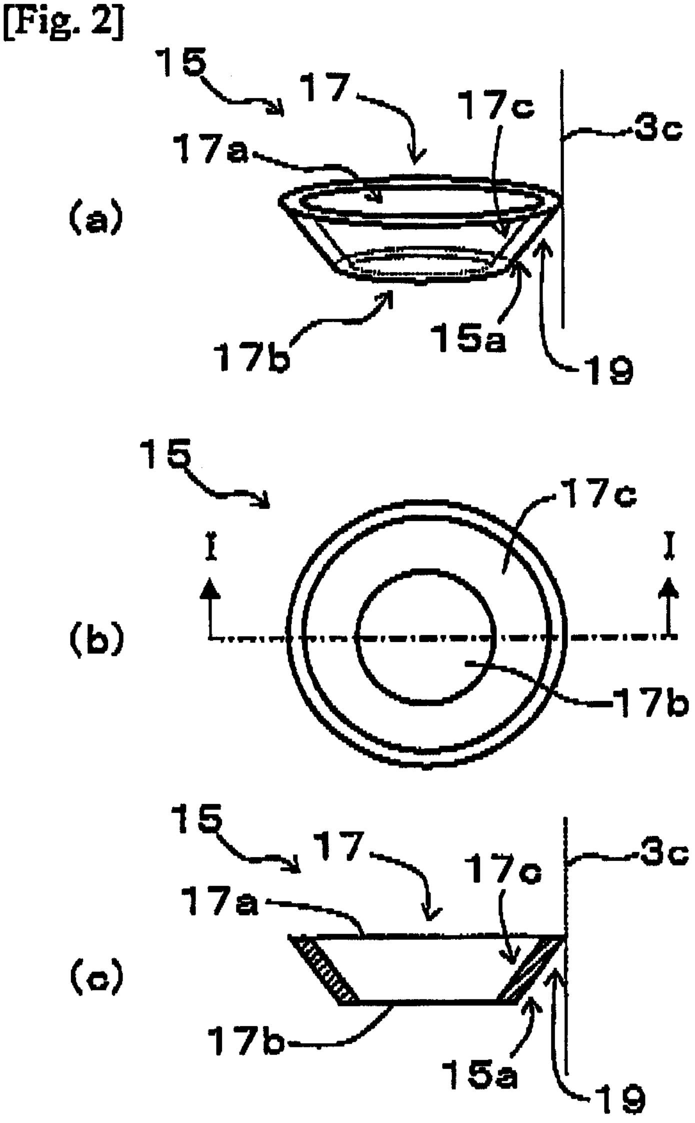

[Fig. 3]
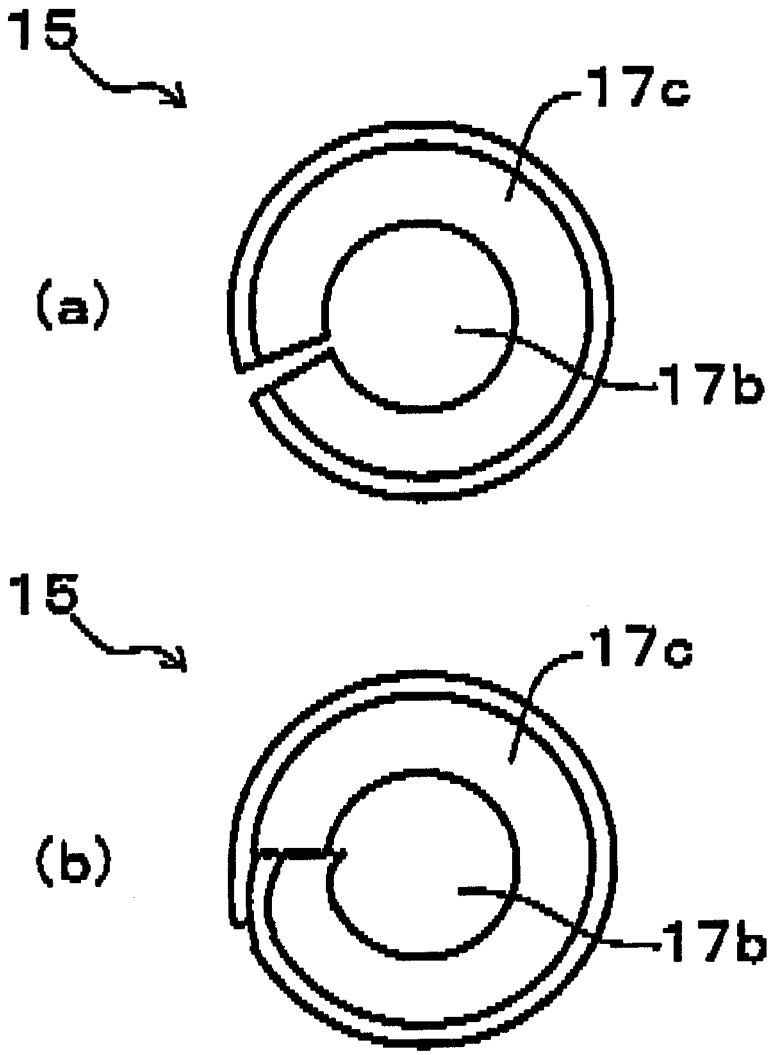

[Fig. 4]
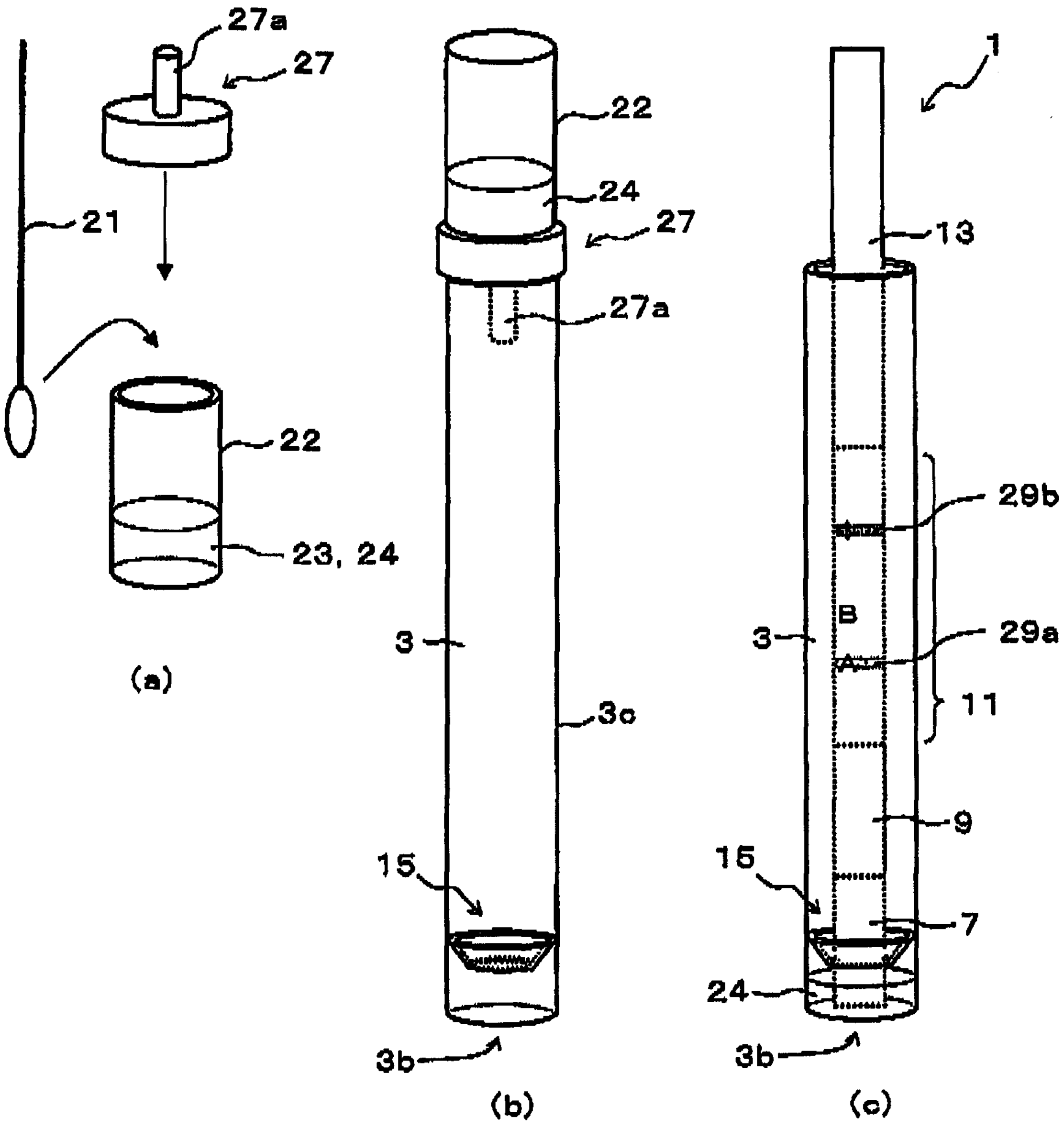

[Fig. 5]
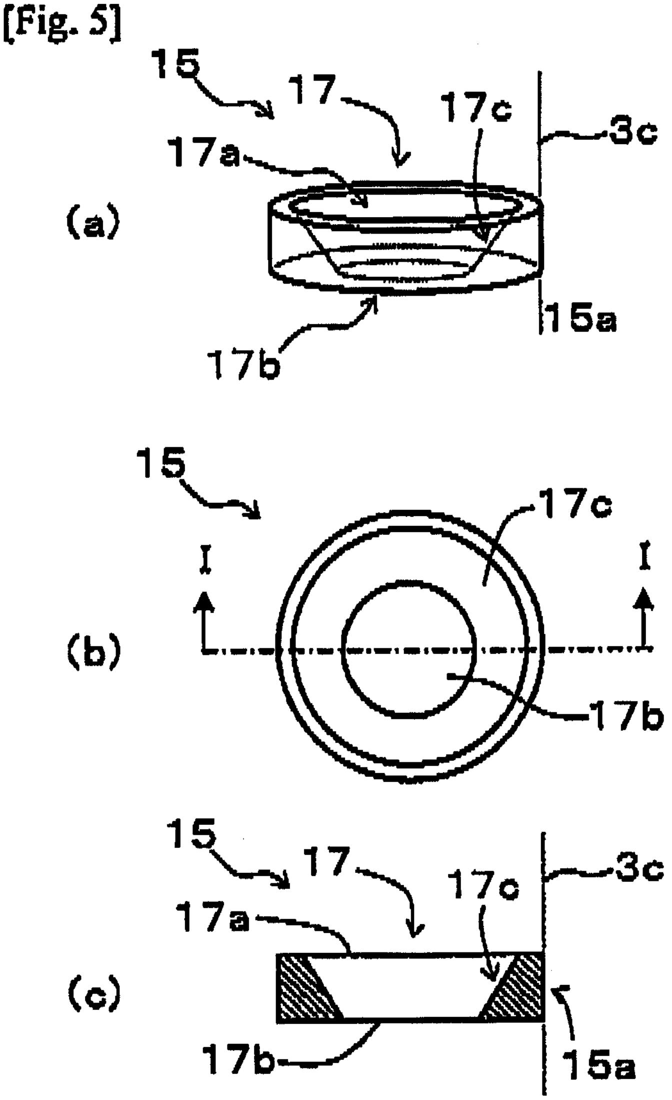

[Fig. 6]
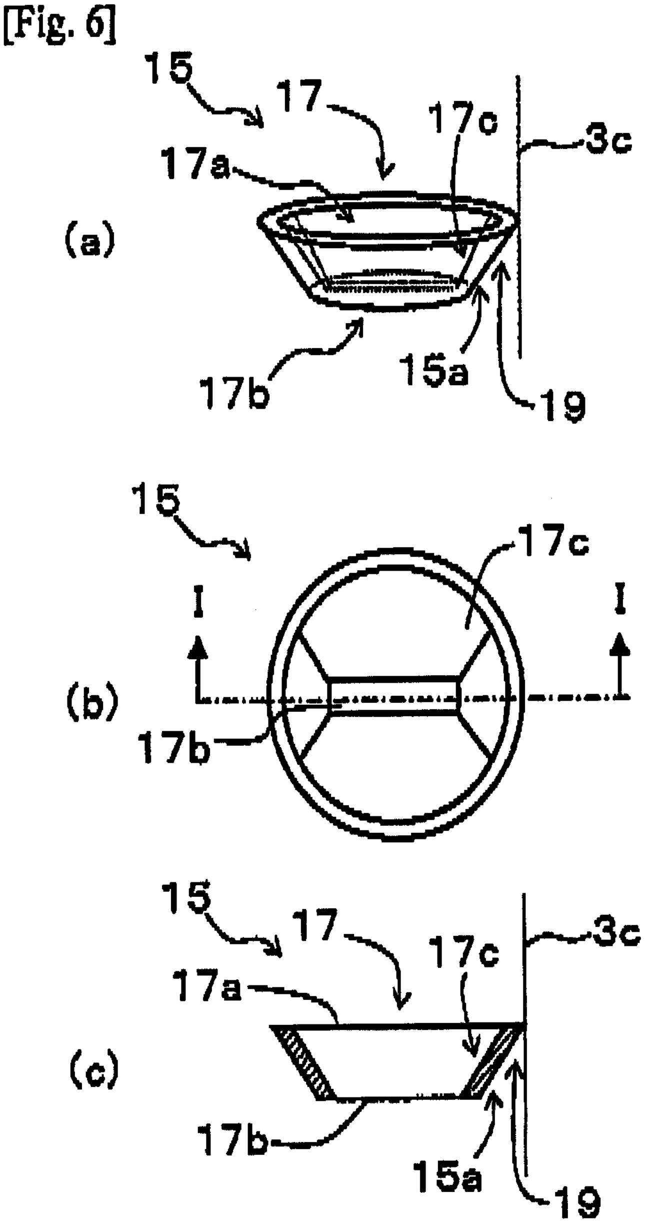

[Fig.7]
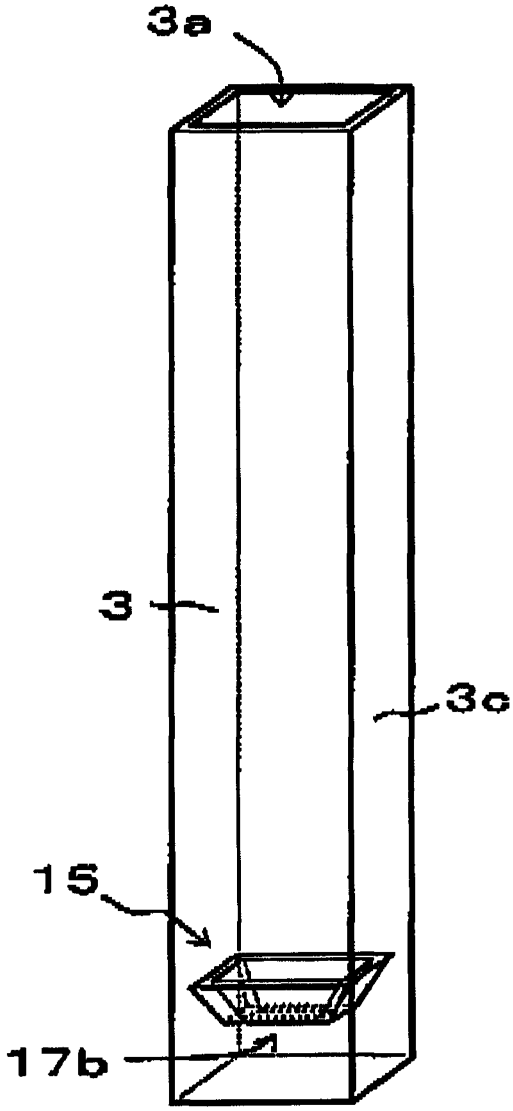

[Fig. 8]
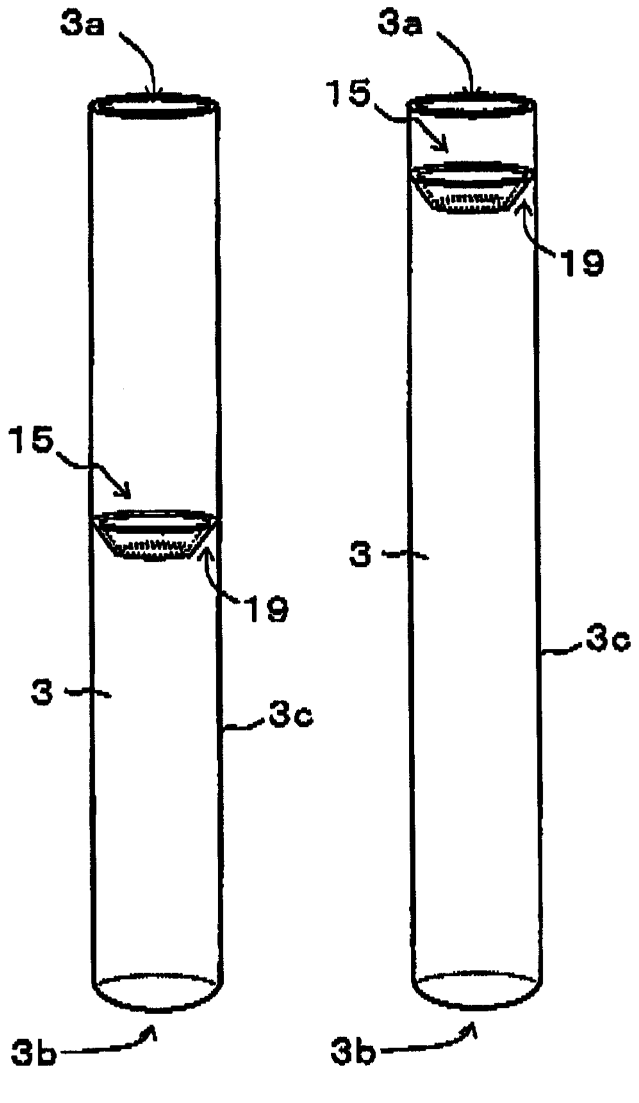

[Fig. 9]
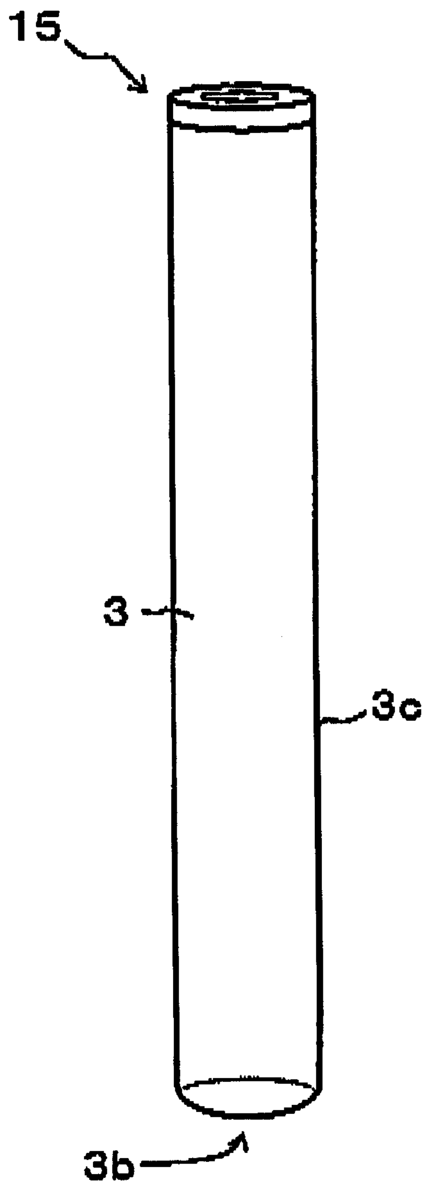

[Fig. 10]
(a)
(b)
(c)
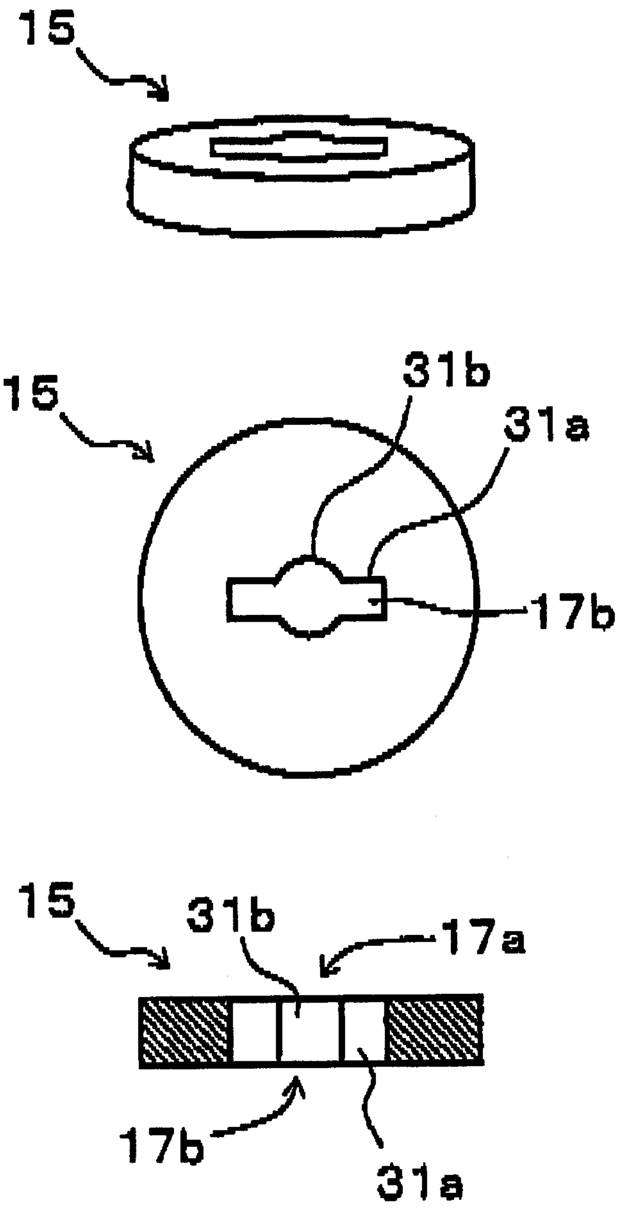

[Fig. 11]
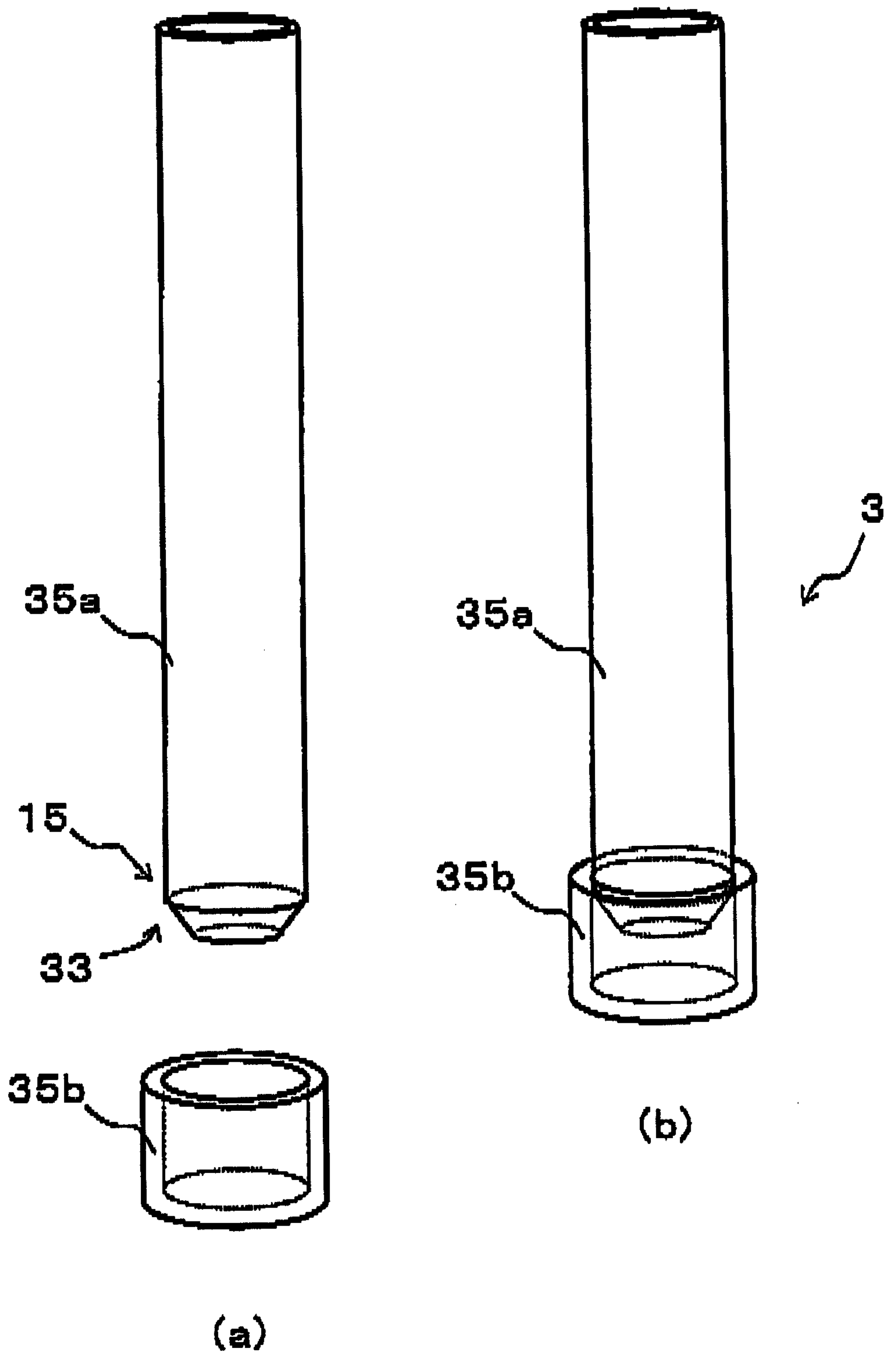

[Fig. 12]
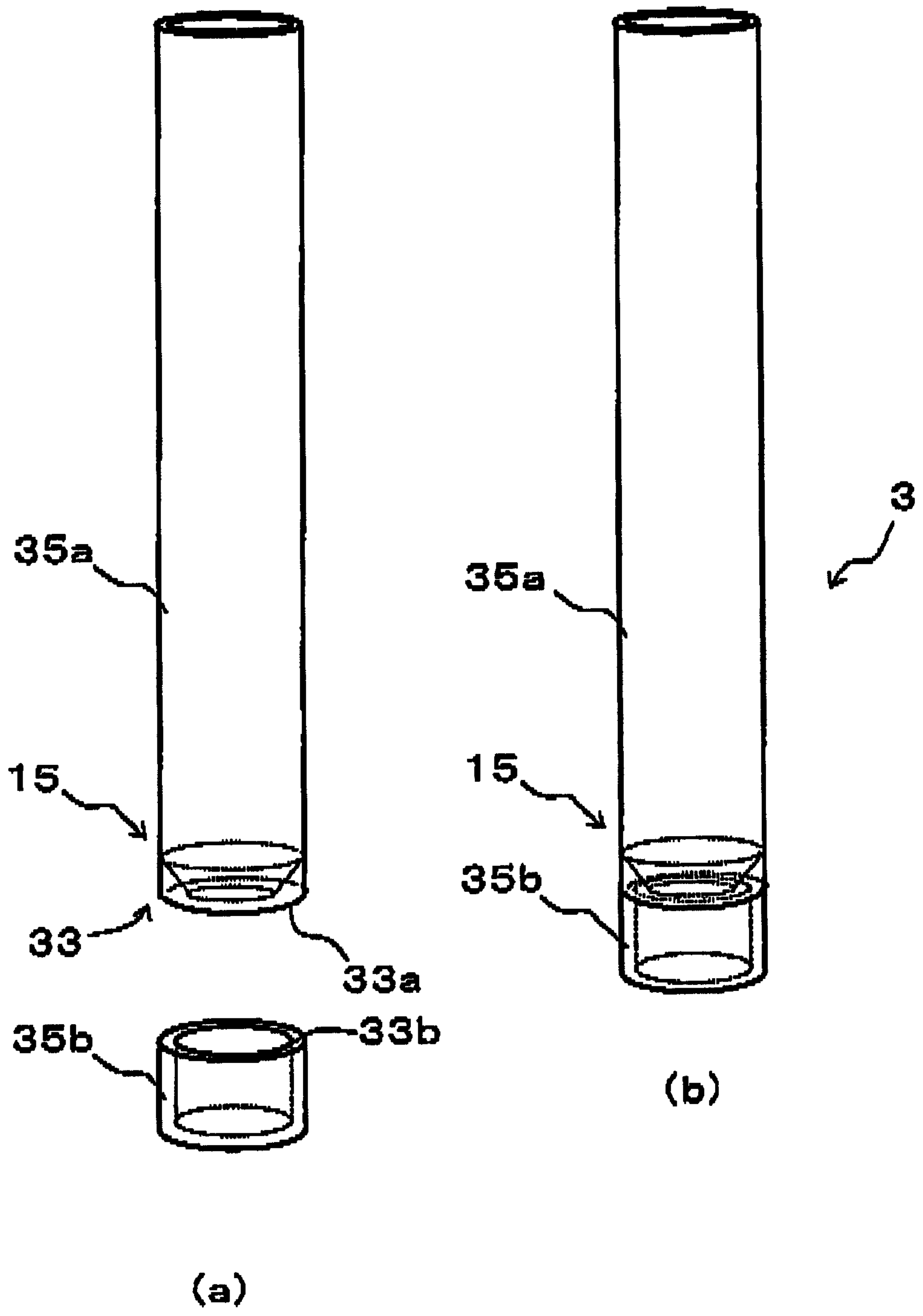

[Fig. 14]
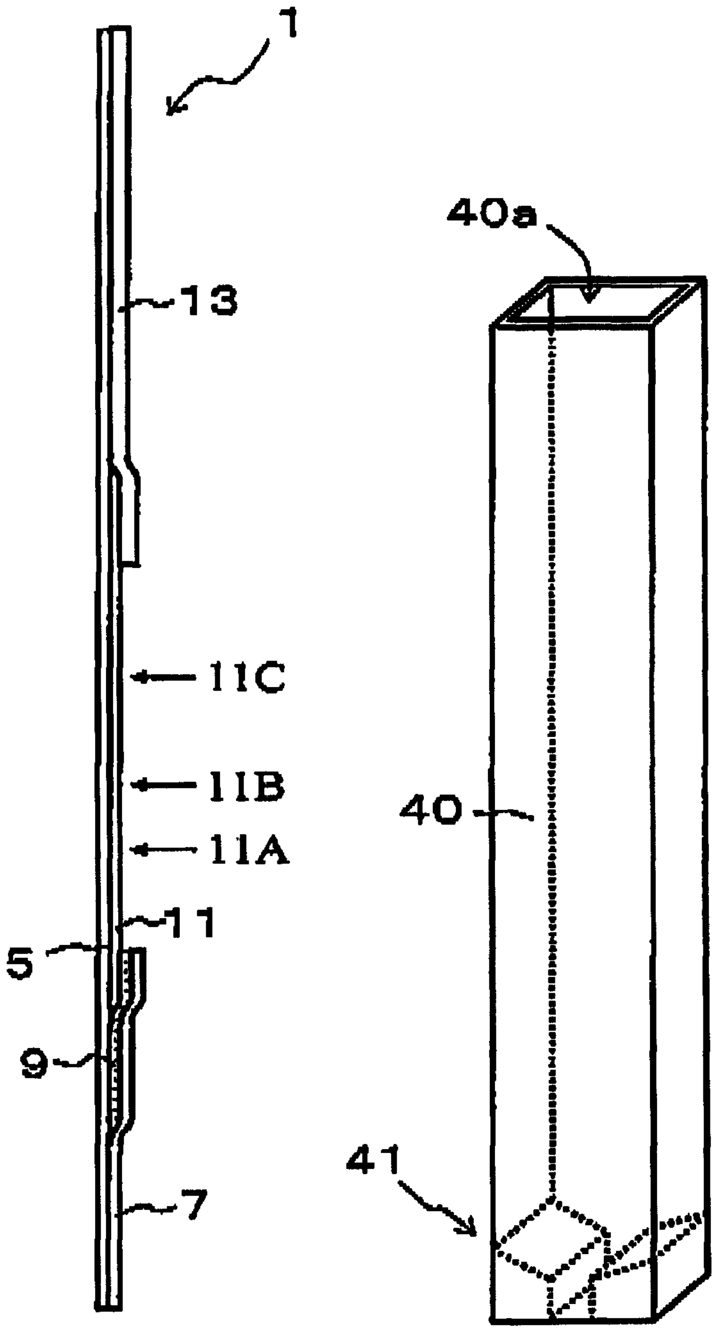

[Fig. 15]
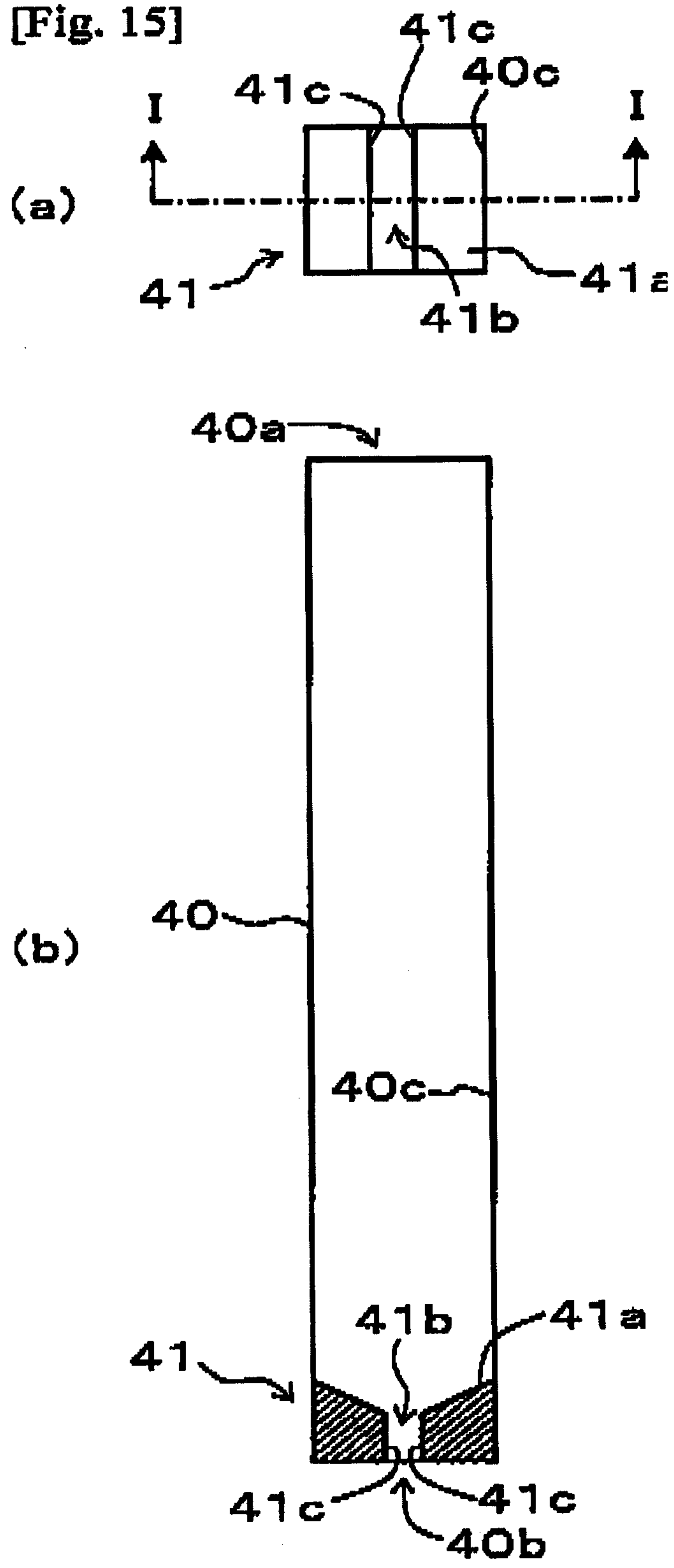

[Fig. 17]
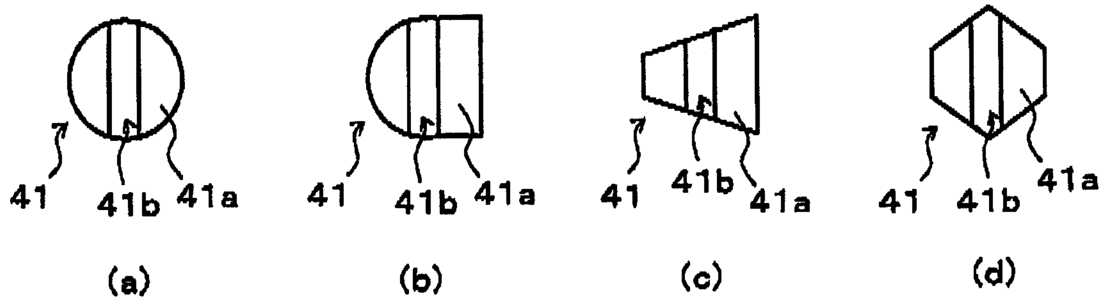

[Fig. 18]
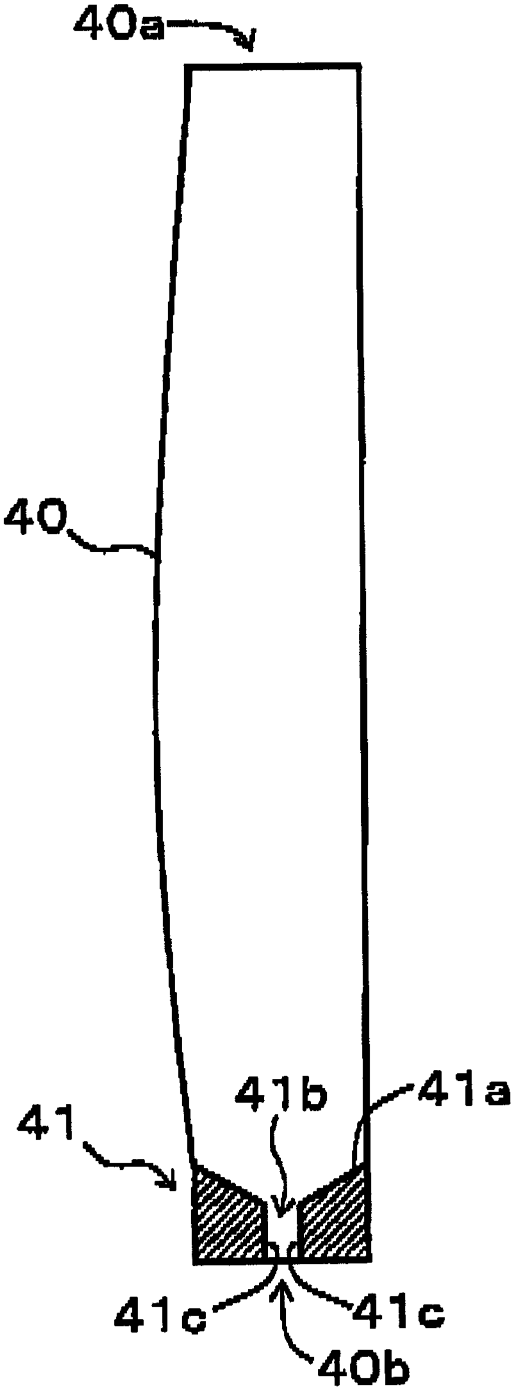

[Fig. 19]
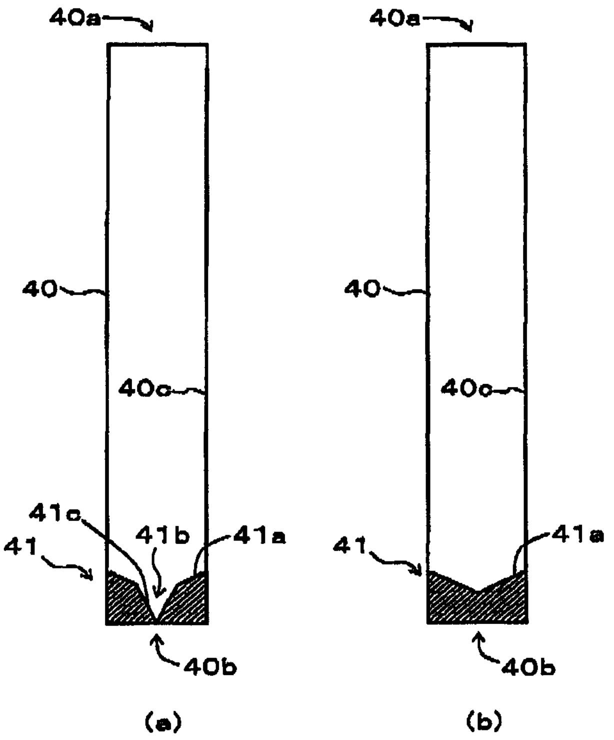

[Fig. 20]
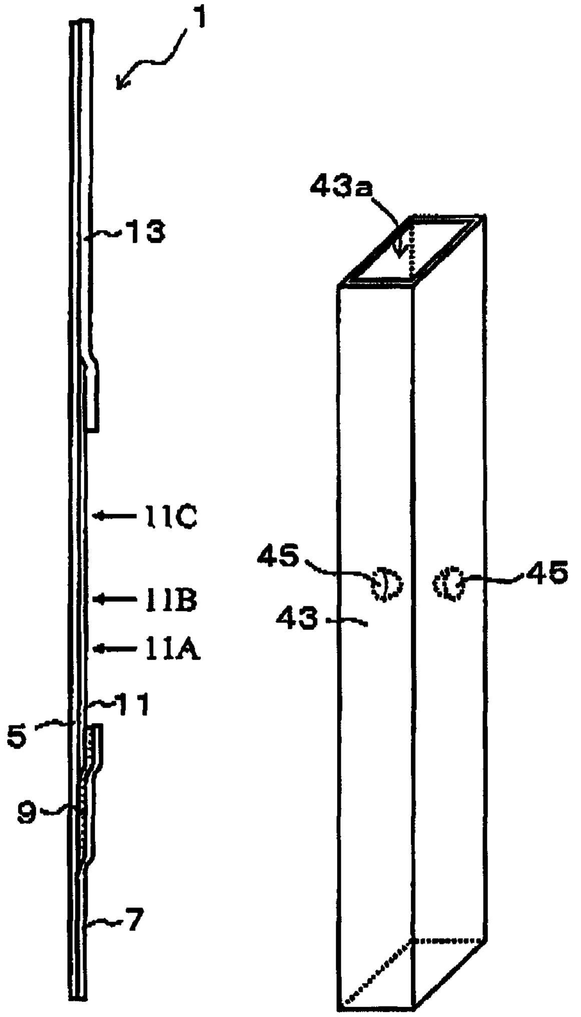

[Fig. 21]
(a)
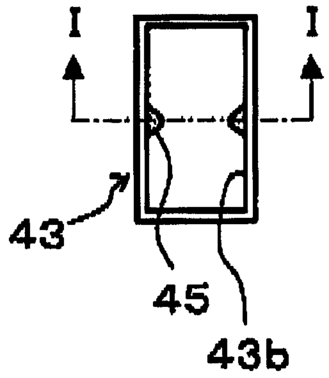
(b)
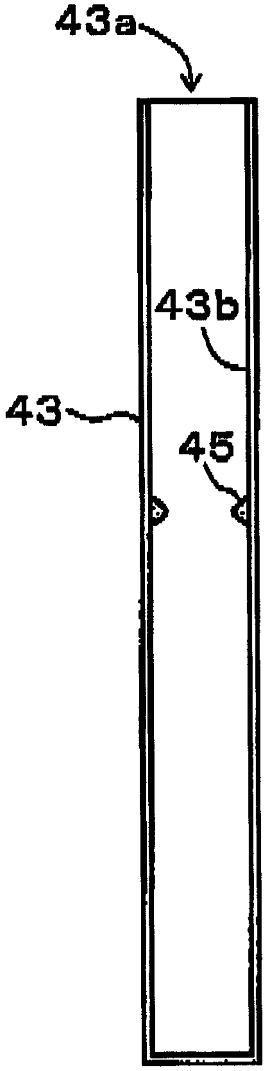

[Fig. 22]
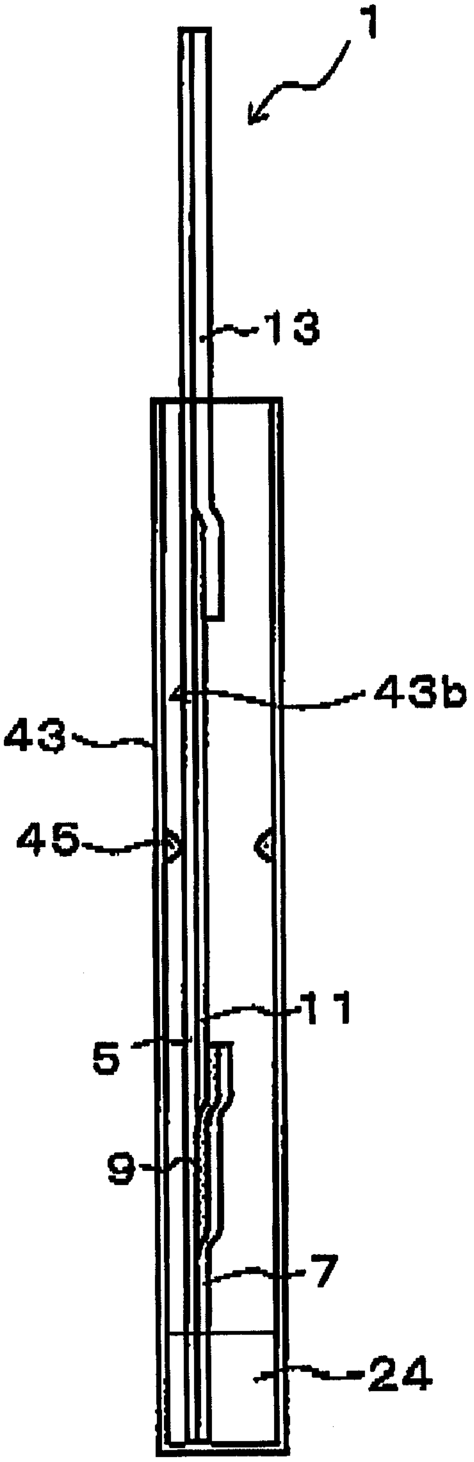

[Fig. 23]
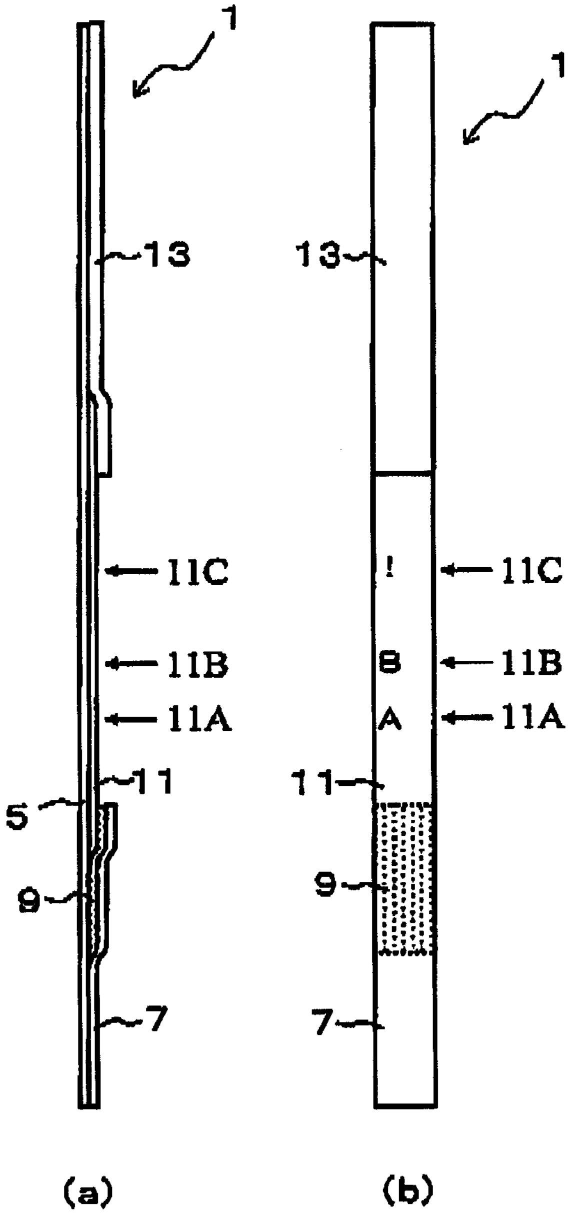

[Fig. 24]
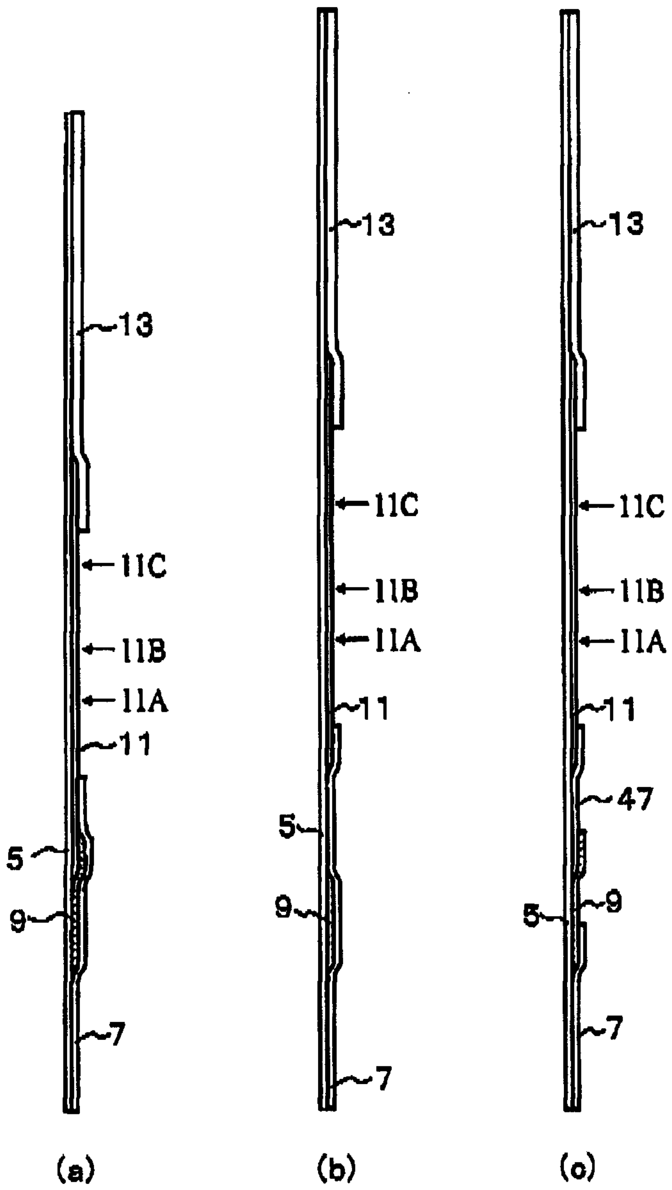

[Fig. 16]
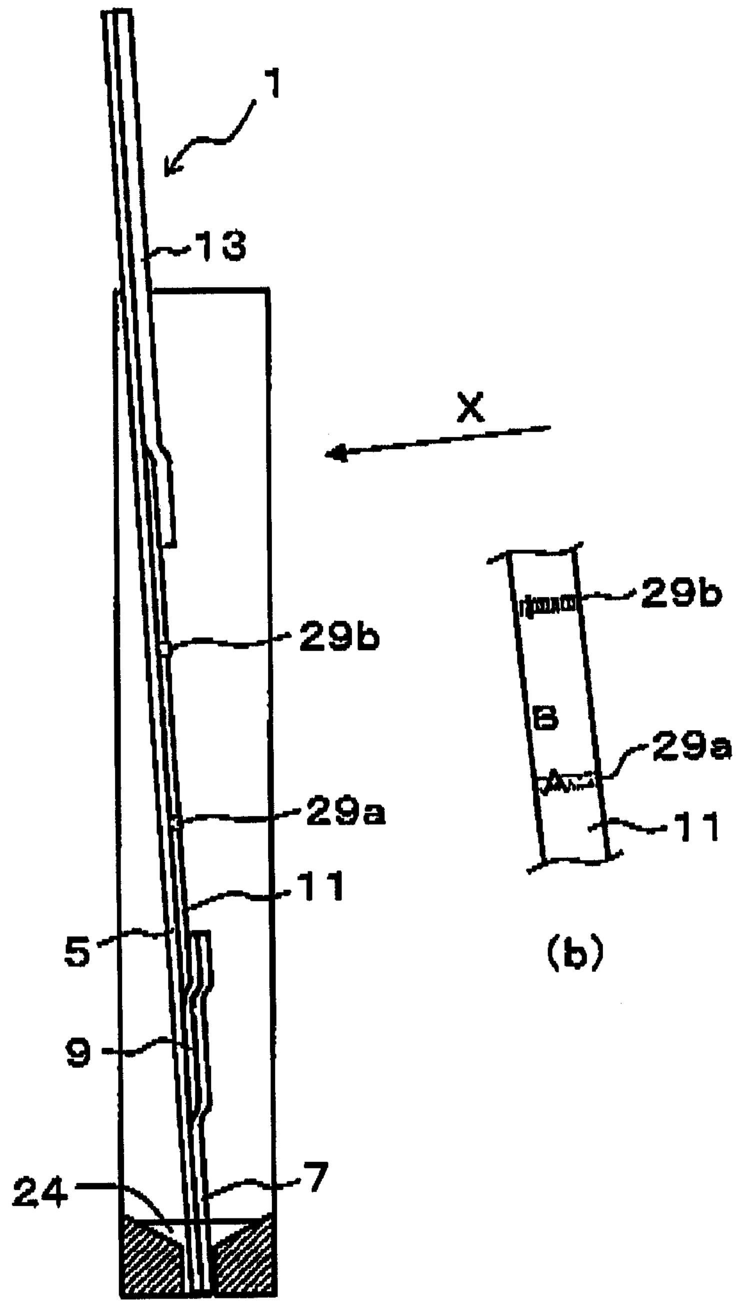
(a)
(b)